United States Patent
Torikai et al.

(10) Patent No.: US 12,220,457 B2
(45) Date of Patent: Feb. 11, 2025

(54) MODIFIED CMV gB PROTEIN AND CMV VACCINE INCLUDING SAME

(71) Applicant: KM Biologics Co., Ltd., Kumamoto (JP)

(72) Inventors: Masaharu Torikai, Kumamoto (JP); Hiroaki Mori, Kumamoto (JP); Tomohiro Nishimura, Kumamoto (JP); Miyuki Matsumoto, Kumamoto (JP); Hiroyuki Shimizu, Saitama (JP); Akihiro Koube, Kumamoto (JP); Takamasa Nagatomo, Kumamoto (JP); Naoki Inoue, Gifu (JP)

(73) Assignee: KM Biologics Co., Ltd., Kumamoto (JP)

( * ) Notice: Subject to any disclaimer, the term of this patent is extended or adjusted under 35 U.S.C. 154(b) by 859 days.

(21) Appl. No.: 17/285,874

(22) PCT Filed: Oct. 24, 2019

(86) PCT No.: PCT/JP2019/041784
§ 371 (c)(1),
(2) Date: Apr. 15, 2021

(87) PCT Pub. No.: WO2020/085457
PCT Pub. Date: Apr. 30, 2020

(65) Prior Publication Data
US 2021/0346494 A1    Nov. 11, 2021

(30) Foreign Application Priority Data
Oct. 25, 2018    (JP) .................................. 2018-201201

(51) Int. Cl.
*A61K 39/25*    (2006.01)
*C12N 7/00*    (2006.01)

(52) U.S. Cl.
CPC ................ *A61K 39/25* (2013.01); *C12N 7/00* (2013.01); *C12N 2710/16134* (2013.01)

(58) Field of Classification Search
CPC ........ A61K 39/245; A61P 31/22; A61P 37/04; C12N 2710/16122; C07K 14/005
See application file for complete search history.

(56) References Cited

U.S. PATENT DOCUMENTS

| | | | |
|---|---|---|---|
| 2011/0182897 A1 | 7/2011 | Hultberg et al. | |
| 2017/0101630 A1 | 4/2017 | Minshull et al. | |

FOREIGN PATENT DOCUMENTS

| | | |
|---|---|---|
| CA | 2583716 A1 | 10/2008 |
| CN | 101054415 A | 10/2007 |
| CN | 101397334 A | 4/2009 |
| CN | 102816246 A | 12/2012 |
| CN | 110506060 A | 11/2019 |
| CN | 113164585 A | 7/2021 |
| CN | 115698298 A | 2/2023 |
| JP | 3-503478 A | 8/1991 |
| JP | H10113192 A | 5/1998 |
| JP | 2014-501491 A | 1/2014 |
| JP | 20140007404 A | 1/2014 |
| JP | 2015-524271 A | 8/2015 |
| WO | 89/07143 A1 | 8/1989 |
| WO | 2012/047732 A2 | 4/2012 |
| WO | 2012/049317 A2 | 4/2012 |
| WO | 2014/018117 A1 | 1/2014 |
| WO | 2015089340 A1 | 6/2015 |
| WO | 2016092460 A2 | 6/2016 |
| WO | 2021/251384 A1 | 12/2021 |

OTHER PUBLICATIONS

Patent Cooperation Treaty, International Preliminary Report on Patentability issued in PCT/JP2019/041784, Jan. 21, 2020, pp. 1-11.
Patent Cooperation Treaty, International Search Report issued in PCT/JP2019/041784, Jan. 21, 2020, pp. 1-3.
Takanashi et al., "Cytomegalovirus seropositivity in pregnant women in Japan during 1996-2009", Journal of Japan Society Perinatal and Neonatal Medicine, Dec. 2010, pp. 1273-1279, vol. 46(4), English abstract p. 9 of PDF.
Tanimura et al., "Universal Screening With Use of Immunoglobulin G Avidity for Congenital Cytomegalovirus Infection", Clinical Infectious Diseases, CID 2017:65, Nov. 2015, pp. 1652-1658.
Stratton et al., "Vaccines for the 21st Century: A Tool for Decisionmaking", The National Academies Press, 2000, pp. 1-473, Washington, D.C.
Revello et al., "A Randomized Trial of Hyperimmune Globulin to Prevent Congenital Cytomegalovirus", The New England Journal of Medicine, Apr. 3, 2014, pp. 1316-1326, vol. 370(14).
Pass et al., "Vaccine Prevention of Maternal Cytomegalovirus Infection", New England Journal of Medicine, Mar. 19, 2009, pp. 1191-1199, vol. 360(12).
Tobin et al., "Deceptive imprinting and immune refocusing in vaccine design.", Vaccine, 2008, pp. 6189-6199, vol. 26.
Potzsch et al., "B Cell Repertoire Analysis Identifies New Antigenic Domains on Glycoprotein B of Human Cytomegalovirus which Are Target of Neutralizing Antibodies", PLoS Pathogens, Aug. 2011, pp. 1-14, vol. 7(8), e1002172.

(Continued)

*Primary Examiner* — Bao Q Li
(74) *Attorney, Agent, or Firm* — Pillsbury Winthrop Shaw Pittman LLP (CV)

(57) ABSTRACT

The present invention is directed to provide a modified CMV gB protein that can induce a group of antibodies including a high ratio of neutralizing antibodies that exhibit a high neutralizing activity against a CMV gB protein, in comparison with a wild type CMV gB, upon induction of immunity and that can be used in the prevention and/or treatment of CMV infection and a CMV vaccine comprising the modified CMV gB protein. The modified CMV gB protein according to the present invention is a modified CMV gB protein having an improved ability to induce body region-recognizing antibodies and comprising modification in a head region.

6 Claims, 11 Drawing Sheets
Specification includes a Sequence Listing.

(56) References Cited

OTHER PUBLICATIONS

Burke et al., "Crystal Structure of the Human Cytomegalovirus Glycoprotein B", PLoS Pathogens, DOI:10.1371/journal.ppat.1005227, Oct. 20, 2015, pp. 1-21.

Yu et al., "Replacing the decoy epitope of PCV2b capsid protein with a protective epitope enhances efficacy of PCV2b vaccine", Vaccine, 2016, pp. 6358-6366, vol. 34.

Cleveland et al., "Immunogenic and Antigenic Dominance of a Nonneutralizing Epitope over a Highly Conserved Neutralizing Epitope in the gp41 Envelope Glycoprotein of Human Immunodeficiency Virus Type 1: Its Deletion Leads to a Strong Neutralizing Response", Virology, 2000, pp. 66-78, vol. 266.

Nara et al., "How Can Vaccines Against Influenza and Other Viral Diseases Be Made More Effective?", PLoS Biology, Dec. 2010, pp. 1-4, vol. 8(12) e1000571.

Cleveland et al, "Immunogenic and antigenic dominance of a nonneutralizing epitope over a highly conserved neutralizing epitope in the gp41 envelope glycoprotein of human immunodeficiency virus type 1: Its deletion leads to a strong neutralizing response", Virology, Dec. 31, 2000, pp. 66-78, vol. 266.

Nara et al, "How can vaccines against influenza and other viral diseases be made more effective?", PLos Biology, Aug. 31, 2010, pp. 1-4, vol. 8(12).

Lilleri et al., "Fetal Human Cytomegalovirus Transmission Correlates with Delayed Maternal Antibodies to gH/gL/pUL128-130-131 Complex during Primary Infection", PLOS One, Mar. 2013, pp. 1-13, e59863, vol. 8(3).

Chatterjee et al., "Modification of Maternal and Congenital Cytomegalovirus Infection by Anti-Glycoprotein B Antibody Transfer in Guinea Pigs", The Journal of Infectious Diseases, Jun. 1, 2001, pp. 1547-1553, vol. 183.

(a)

(b)

(a)

(b)

(a)

(b)

(a)

(b)

(a)

(b)

(c)

(a)

(b)

(b)

(c)

SEQUENCE LISTING

```
<160> NUMBER OF SEQ ID NOS: 3

<210> SEQ ID NO 1
<211> LENGTH: 882
<212> TYPE: PRT
<213> ORGANISM: human cytomegalovirus

<400> SEQUENCE: 1

Ser Ser Ser Thr Ser His Ala Thr Ser Ser Thr His Asn Gly Ser His
1               5                   10                  15

Thr Ser Arg Thr Thr Ser Ala Gln Thr Arg Ser Val Tyr Ser Gln His
            20                  25                  30

Val Thr Ser Ser Glu Ala Val Ser His Arg Ala Asn Glu Thr Ile Tyr
        35                  40                  45

Asn Thr Thr Leu Lys Tyr Gly Asp Val Val Gly Val Asn Thr Thr Lys
    50                  55                  60

Tyr Pro Tyr Arg Val Cys Ser Met Ala Gln Gly Thr Asp Leu Ile Arg
```

```
                65                  70                  75                  80
           Phe Glu Arg Asn Ile Ile Cys Thr Ser Met Lys Pro Ile Asn Glu Asp
                            85                  90                  95
           Leu Asp Glu Gly Ile Met Val Val Tyr Lys Arg Asn Ile Val Ala His
                           100                 105                 110
           Thr Phe Lys Val Arg Val Tyr Gln Lys Val Leu Thr Phe Arg Arg Ser
                           115                 120                 125
           Tyr Ala Tyr Ile Tyr Thr Thr Tyr Leu Leu Gly Ser Asn Thr Glu Tyr
                           130                 135                 140
           Val Ala Pro Pro Met Trp Glu Ile His His Ile Asn Lys Phe Ala Gln
           145                 150                 155                 160
           Cys Tyr Ser Ser Tyr Ser Arg Val Ile Gly Gly Thr Val Phe Val Ala
                           165                 170                 175
           Tyr His Arg Asp Ser Tyr Glu Asn Lys Thr Met Gln Leu Ile Pro Asp
                           180                 185                 190
           Asp Tyr Ser Asn Thr His Ser Thr Arg Tyr Val Thr Val Lys Asp Gln
                           195                 200                 205
           Trp His Ser Arg Gly Ser Thr Trp Leu Tyr Arg Glu Thr Cys Asn Leu
                           210                 215                 220
           Asn Cys Met Leu Thr Ile Thr Thr Ala Arg Ser Lys Tyr Pro Tyr His
           225                 230                 235                 240
           Phe Phe Ala Thr Ser Thr Gly Asp Val Val Tyr Ile Ser Pro Phe Tyr
                           245                 250                 255
           Asn Gly Thr Asn Arg Asn Ala Ser Tyr Phe Gly Glu Asn Ala Asp Lys
                           260                 265                 270
           Phe Phe Ile Phe Pro Asn Tyr Thr Ile Val Ser Asp Phe Gly Arg Pro
                           275                 280                 285
           Asn Ala Ala Pro Glu Thr His Arg Leu Val Ala Phe Leu Glu Arg Ala
                           290                 295                 300
           Asp Ser Val Ile Ser Trp Asp Ile Gln Asp Glu Lys Asn Val Thr Cys
           305                 310                 315                 320
           Gln Leu Thr Phe Trp Glu Ala Ser Glu Arg Thr Ile Arg Ser Glu Ala
                           325                 330                 335
           Glu Asp Ser Tyr His Phe Ser Ser Ala Lys Met Thr Ala Thr Phe Leu
                           340                 345                 350
           Ser Lys Lys Gln Glu Val Asn Met Ser Asp Ser Ala Leu Asp Cys Val
                           355                 360                 365
           Arg Asp Glu Ala Ile Asn Lys Leu Gln Gln Ile Phe Asn Thr Ser Tyr
                           370                 375                 380
           Asn Gln Thr Tyr Glu Lys Tyr Gly Asn Val Ser Val Phe Glu Thr Ser
           385                 390                 395                 400
           Gly Gly Leu Val Val Phe Trp Gln Gly Ile Lys Gln Lys Ser Leu Val
                           405                 410                 415
           Glu Leu Glu Arg Leu Ala Asn Arg Ser Ser Leu Asn Ile Thr His Arg
                           420                 425                 430
           Thr Arg Arg Ser Thr Ser Asp Asn Asn Thr Thr His Leu Ser Ser Met
                           435                 440                 445
           Glu Ser Val His Asn Leu Val Tyr Ala Gln Leu Gln Phe Thr Tyr Asp
                           450                 455                 460
           Thr Leu Arg Gly Tyr Ile Asn Arg Ala Leu Ala Gln Ile Ala Glu Ala
           465                 470                 475                 480
           Trp Cys Val Asp Gln Arg Arg Thr Leu Glu Val Phe Lys Glu Leu Ser
                           485                 490                 495
```

```
Lys Ile Asn Pro Ser Ala Ile Leu Ser Ala Ile Tyr Asn Lys Pro Ile
            500                 505                 510

Ala Ala Arg Phe Met Gly Asp Val Leu Gly Leu Ala Ser Cys Val Thr
            515                 520                 525

Ile Asn Gln Thr Ser Val Lys Val Leu Arg Asp Met Asn Val Lys Glu
            530                 535                 540

Ser Pro Gly Arg Cys Tyr Ser Arg Pro Val Val Ile Phe Asn Phe Ala
545                 550                 555                 560

Asn Ser Ser Tyr Val Gln Tyr Gly Gln Leu Gly Glu Asp Asn Glu Ile
                565                 570                 575

Leu Leu Gly Asn His Arg Thr Glu Glu Cys Gln Leu Pro Ser Leu Lys
            580                 585                 590

Ile Phe Ile Ala Gly Asn Ser Ala Tyr Glu Tyr Val Asp Tyr Leu Phe
            595                 600                 605

Lys Arg Met Ile Asp Leu Ser Ser Ile Ser Thr Val Asp Ser Met Ile
            610                 615                 620

Ala Leu Asp Ile Asp Pro Leu Glu Asn Thr Asp Phe Arg Val Leu Glu
625                 630                 635                 640

Leu Tyr Ser Gln Lys Glu Leu Arg Ser Ser Asn Val Phe Asp Leu Glu
                645                 650                 655

Glu Ile Met Arg Glu Phe Asn Ser Tyr Lys Gln Arg Val Lys Tyr Val
            660                 665                 670

Glu Asp Lys Val Val Asp Pro Leu Pro Pro Tyr Leu Lys Gly Leu Asp
            675                 680                 685

Asp Leu Met Ser Gly Leu Gly Ala Ala Gly Lys Ala Val Gly Val Ala
            690                 695                 700

Ile Gly Ala Val Gly Gly Ala Val Ala Ser Val Val Glu Gly Val Ala
705                 710                 715                 720

Thr Phe Leu Lys Asn Pro Phe Gly Ala Phe Thr Ile Ile Leu Val Ala
                725                 730                 735

Ile Ala Val Val Ile Ile Thr Tyr Leu Ile Tyr Thr Arg Gln Arg Arg
            740                 745                 750

Leu Cys Thr Gln Pro Leu Gln Asn Leu Phe Pro Tyr Leu Val Ser Ala
            755                 760                 765

Asp Gly Thr Thr Val Thr Ser Gly Ser Thr Lys Asp Thr Ser Leu Gln
            770                 775                 780

Ala Pro Pro Ser Tyr Glu Glu Ser Val Tyr Asn Ser Gly Arg Lys Gly
785                 790                 795                 800

Pro Gly Pro Pro Ser Ser Asp Ala Ser Thr Ala Ala Pro Pro Tyr Thr
                805                 810                 815

Asn Glu Gln Ala Tyr Gln Met Leu Leu Ala Leu Ala Arg Leu Asp Ala
            820                 825                 830

Glu Gln Arg Ala Gln Gln Asn Gly Thr Asp Ser Leu Asp Gly Gln Thr
            835                 840                 845

Gly Thr Gln Asp Lys Gly Gln Lys Pro Asn Leu Leu Asp Arg Leu Arg
            850                 855                 860

His Arg Lys Asn Gly Tyr Arg His Leu Lys Asp Ser Asp Glu Glu Glu
865                 870                 875                 880

Asn Val

<210> SEQ ID NO 2
<211> LENGTH: 9
<212> TYPE: PRT
```

```
<213> ORGANISM: Artificial Sequence
<220> FEATURE:
<223> OTHER INFORMATION: linker

<400> SEQUENCE: 2

Gly Gly Gly Ser Gly Ser Gly Gly Gly
1               5

<210> SEQ ID NO 3
<211> LENGTH: 10
<212> TYPE: PRT
<213> ORGANISM: Artificial Sequence
<220> FEATURE:
<223> OTHER INFORMATION: linker

<400> SEQUENCE: 3

Gly Gly Gly Gly Ser Gly Gly Gly Gly Ser
1               5                   10
```

MODIFIED CMV gB PROTEIN AND CMV VACCINE INCLUDING SAME

RELATED PATENT APPLICATIONS

This application is based on and claims the benefit of priority from International Application No. PCT/JP2019/041784, filed on Oct. 24, 2019, which claims priority to Japanese Patent Application No. 2018-201201, filed on Oct. 25, 2018, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 8, 2021, is named "FP19-0912-00_Amended_Sequence_Listing.txt" and is 7.85 KB in size.

TECHNICAL FIELD

The present invention relates to a modified CMV gB protein and a CMV vaccine comprising the modified CMV gB protein.

BACKGROUND ART

Human cytomegalovirus (CMV) infections mainly include major two: organ dysfunctions such as CMV pneumonia, enteritis, and retinitis, which develop in patients in immunocompromised states such as transplantation, AIDS, and congenital immunodeficiency; and congenital CMV infections, which develop in a fetus when a pregnant woman is infected for the first time. Of these, the congenital CMV infection is an important congenital infection constituting one of the TORCH syndrome and causes malformation or severe clinical manifestations in fetuses. When pregnant women are infected with CMV for the first time, the congenital infection occurs in approximately 40% of the fetuses via the placenta. Moreover, there is a report that approximately 15% of stillbirths are due to congenital CMV infection. The annual number of occurrences of infants with congenital infection is 3000 or more in Japan and approximately 40000 in the United States, and symptomatic ones are said to be approximately 1000 in Japan and approximately 8000 in the United States, of which postinfectious disorders, such as central nerve disorders and hearing loss persist in approximately 90% of them.

The CMV seropositive rate in Japan is higher than those in North American and European countries, 80% to 90% of Japanese adults are CMV seropositive and most people are infected in infancy. However, the CMV seropositive rate in young people has shown a decreasing tendency from the 90-100% range to the 60-70% range, as a recent tendency, and the need of prophylaxis against congenital CMV infection has further increased (Non Patent Literature 1).

There is also a report, from a very recent study, that infants with congenital CMV infection, who have been so far considered to be born more from mothers who had the first infection during pregnancy, have been born more from pregnant women in a chronic infection state than from pregnant women who had the first infection during pregnancy (Non Patent Literature 2).

The Institute of Medicine in the United States has made an analysis that congenital CMV infection has an impact exceeding Down syndrome as a cause of congenital central nerve disorders in developed countries and CMV vaccines are classified in the category with the highest medical economic cost-effectiveness on the basis of the calculation of decrease in lifetime QOL for infants with congenital infection who had lasting disorders and socioeconomic loss as QALYs (Quality-adjusted life years) (Non Patent Literature 3).

Pathogens that cause infection are classified roughly into Class I pathogens, of which conventional vaccines can yield sufficient effects, and Class II pathogens, of which sufficient protective immunity cannot be acquired by conventional vaccines or history of infection with the pathogen, and CMV is classified in the latter (Non Patent Literature 4). It is indicated to be a reason for the difficulty of conquest over Class II pathogens that they have sophisticated mechanisms of escaping the immunity. Humankind has so far developed many effective vaccines against Class I pathogens and defeated the menace of infections that they cause. The focus of future vaccine development is moving to Class II pathogens.

To address CMV-related diseases, development of vaccines including attenuated live vaccines and subunit vaccines has been conducted. Patent Literature 1 to 3 disclose vaccines for modified type CMV envelope glycoprotein B (gB).

To minimize the damage of congenital CMV infection, identification of uninfected pregnant women by screening of pregnant women and enlightenment of them to take in daily life are conducted, but they are not enough. Furthermore, although there appears to be a report claiming that it was effective for prevention of infection and reduction of aggravation in fetuses to identify pregnant women with infection for the first time and administer an anti-CMV hyperimmunoglobulin to the pregnant women, its efficacy is currently being questioned (Non Patent Literature 5).

Antiviral drugs such as aciclovir are used in treatment against CMV. However, these antiviral drugs cannot completely remove viruses and viruses are reactivated when their administration is stopped. Ganciclovir has also been marketed as a small molecule drug, but its effect is limited and there are problems of side effects. Therefore, the development of a preventive vaccine for protecting against infection itself of CMV or a therapeutic vaccine that reduces or alleviates recurrent symptoms is desired, but currently an effective vaccine does not exist, and its unmet needs are high.

About CMV vaccine development, studies using attenuated live vaccines, adjuvanted recombinant protein vaccines, DNA vaccines, and the like have so far been attempted in a plurality of pharmaceutical companies and academia, but both T-cell immune and B-cell immune responses are insufficient with any of such vaccines and, as a result, an effect that is worthy of practical use as a vaccine has been not gained.

With regard to the bivalent DNA vaccine ASP0113 (gB gene+pp65 gene/Poloxamer CRL1005) under joint development at Astellas Pharma Inc. and Vical Incorporated for the purpose of prevention of CMV infection and its associated complications in organ transplant patients and hematopoietic cell transplant patients, no significant effect relative to that of the placebo group was confirmed in a phase II trial targeted to renal transplant patients. Moreover, no significant effect relative to the placebo group was confirmed also in a phase III trial targeted to hematopoietic cell transplant patients. Moreover, the recombinant protein vaccine (gB/MF59) that Sanofi Pasteur tried to develop for the purpose of prevention of congenital CMV infection exhibited about 50% efficacy in an infection protection test (phase II trial) targeted to uninfected adult women, but its development was stopped because the effect was insufficient (Non Patent Literature 6).

CITATION LIST

Patent Literature

Patent Literature 1: International Publication No. WO 2016/092460
Patent Literature 2: International Publication No. WO 2012/049317
Patent Literature 3: International Publication No. WO 2015/089340

Non Patent Literature

Non Patent Literature 1: Azuma H, Takanashi M, et al., "Cytomegalovirus seropositivity in pregnant women in Japan during 1996-2009," J Jpn Soc Perin Neon Med 46 (2010) 1273-1279
Non Patent Literature 2: Tanimura K et al., "Universal screening with use of Immunoglobulin G avidity for congenital cytomegalovirus infection." Clin Infect Dis 65 (2017) 1652-1658.
Non Patent Literature 3: Kathleen R. Stratton et al., "Vaccines for the 21st century: a tool for decision making" The National Academies Press, 2000
Non Patent Literature 4: Tobin G J et al., "Deceptive imprinting and immune refocusing in vaccine design.", Vaccine 26 (2008) 6189-6199
Non Patent Literature 5: Revello M G et al., "Randomized trial of hyperimmune globulin to prevent congenital cytomegalovirus.", N Engl J Med 370 (2014) 1316-1326
Non Patent Literature 6: Pass R F et al., "Vaccine prevention of maternal cytomegalovirus infection." N Engl J Med 360 (2009) 1191-1199
Non Patent Literature 7: Sonja Potzsch et al., "B cell repertoire analysis identifies new antigenic domains on glycoprotein B of human cytomegalovirus which are target of neutralizing antibodies." PLoS Pathog, 2011; 7 (8): e1002172
Non Patent Literature 8: Burke HG et al., "Crystal structure of the human cytomegalovirus glycoprotein B." PLoS Pathog 2015 Oct. 20, 11 (10): e1005227.

SUMMARY OF INVENTION

Technical Problem

Currently, an effective CMV vaccine does not exist, as described above. Therefore, the present invention is directed to provide a modified CMV gB protein that can induce antibodies including a high ratio of neutralizing antibodies that exhibit a high neutralizing activity against CMV infection, in comparison with a wild type CMV gB, upon induction of immunity and that can be used in the prevention and/or treatment of CMV infection and a CMV vaccine comprising the modified CMV gB protein.

Solution to Problem

The present inventors attempted classifying for a gB protein, which is a main antigen in CMV and known as one of target antigens for preventing infection, into neutralizing epitopes that induce antibodies having high neutralizing activity against CMV infection and nonneutralizing epitopes that induce antibodies with low or no neutralizing activity. Modified CMV gB proteins whose neutralizing antibody inducing ability and ability to prevent infection is increased by deimmunizing the nonneutralizing epitopes to make the neutralizing epitopes immunologically outstanding were found, thereby completing the present invention.

Accordingly, the present invention relates to each of the following inventions.

[1] A modified CMV gB protein comprising a head region modified from a head region in an envelope glycoprotein B (CMV gB protein) in a wild type cytomegalovirus and having an improved ability to induce body region-recognizing antibodies.

[2] The modified CMV gB protein according to [1], wherein the modification in the head region comprises modification by a sugar chain introduction.

[3] The modified CMV gB protein according to [1] or [2], wherein the modification in the head region comprises modification by 2 or more sugar chain introductions.

[4] The modified CMV gB protein according to any one of [1] to [3], wherein the modification in the head region comprises modification by sugar chain introductions to at least 2 amino acid residues selected from the group consisting of amino acid residues at corresponding positions to the positions 77, 544, 588, and 609 in the amino acid sequence set forth in SEQ ID NO: 1.

[5] The modified CMV gB protein according to any one of [1] to [4], wherein the modification in the head region comprises modification by sugar chain introductions to at least 3 amino acid residues selected from the group consisting of amino acid residues at corresponding positions to the positions 77, 544, 588, and 609 in the amino acid sequence set forth in SEQ ID NO: 1.

[6] The modified CMV gB protein according to any one of [1] to [5], wherein the modification in the head region comprises modification by sugar chain introductions to amino acid residues at corresponding positions to the positions 77, 544, and 588 in the amino acid sequence set forth in SEQ ID NO: 1.

[7] The modified CMV gB protein according to any one of [1] to [6], wherein the modification in the head region comprises modification by sugar chain introductions to amino acid residues at corresponding positions to the positions 77, 544, 588, and 609 in the amino acid sequence set forth in SEQ ID NO: 1.

[8] The modified CMV gB protein according to [7], wherein the sugar chain is introduced by substitution of an amino acid residue at a corresponding position to the position 77 in the amino acid sequence set forth in SEQ ID NO: 1 with an asparagine residue and substitution of an amino acid residue at a corresponding position to the position 79 in the amino acid sequence set forth in SEQ ID NO: 1 with a threonine residue, substitution of an amino acid residue at a corresponding position to the position 544 in the amino acid sequence set forth in SEQ ID NO: 1 with an asparagine residue and substitution of an amino acid residue at a corresponding position to the position 546 in the amino acid sequence set forth in SEQ ID NO: 1 with a threonine residue, substitution of an amino acid residue at a corresponding position to the position 588 in the amino acid sequence set forth in SEQ ID NO: 1 with an asparagine residue and substitution of an amino acid residue at a corresponding position to the position 589 in the amino acid sequence set forth in SEQ ID NO: 1 with a glycine residue, and substitution of an amino acid residue at a corresponding position to the position 609 in the amino acid sequence set forth in SEQ ID NO: 1 with an asparagine residue, substitution of an amino acid residue at a corresponding position to the position 610 in the amino acid sequence set forth in SEQ ID NO: 1 with a threonine residue, and substitution of an amino acid residue at a corresponding position to the position 611 in the amino acid sequence set forth in SEQ ID NO: 1 with a threonine residue.

[9] The modified CMV gB protein according to [1], wherein the modification in the head region comprises a deletion of at least part of the head region.

[10] The modified CMV gB protein according to [9], wherein the modification in the head region is a deletion of an entire region of the head region.

[11] The modified CMV gB protein according to [1], wherein the modification in the head region in the CMV gB protein comprises substitution of amino acid residues at corresponding positions to the positions 432 and 434 in the amino acid sequence set forth in SEQ ID NO: 1 and wherein the modified CMV gB protein further comprises modification in a body region and the modification in the body region comprises substitution of amino acid residues at corresponding positions to the positions 132, 133, and 216 in the amino acid sequence set forth in SEQ ID NO: 1.

[12] The modified CMV gB protein according to [11], wherein the modification in the body region further comprises substitution of an amino acid residue at a corresponding position to the position 215 in the amino acid sequence set forth in SEQ ID NO: 1.

[13] The modified CMV gB protein according to [11] or [12], wherein the modification in the body region comprises a deletion of amino acid residues at corresponding positions to the positions from 131 to 133 and the positions from 216 to 218 in the amino acid sequence set forth in SEQ ID NO: 1.

[14] A CMV vaccine comprising the modified CMV gB protein according to any one of [1] to [13].

Advantageous Effects of Invention

When immunity is induced with a modified CMV gB protein according to the present invention or a vaccine comprising the modified CMV gB protein, higher prevention and/or treatment effect against CMV infection can be expected, in comparison with when immunity is induced with a wild type CMV gB.

DESCRIPTION OF EMBODIMENTS

Figure 1:
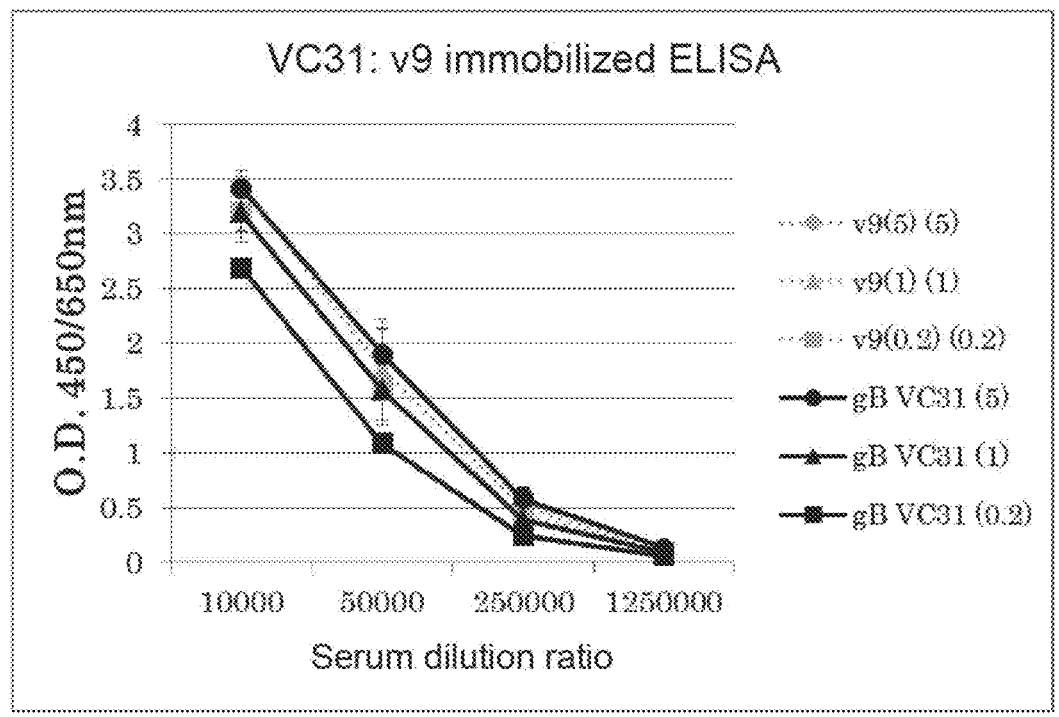
FIG. 1 illustrates a result of immune refocusing from the head region to the body region in Example 6 (VC31).
Figure 1:
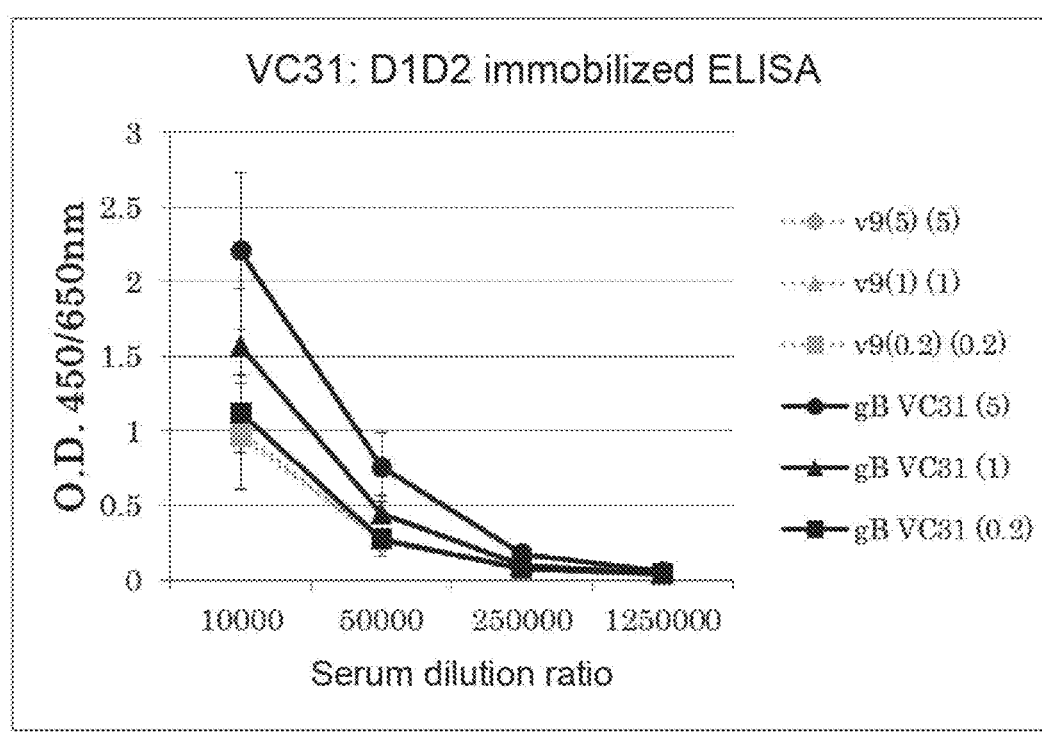
Figure 2:
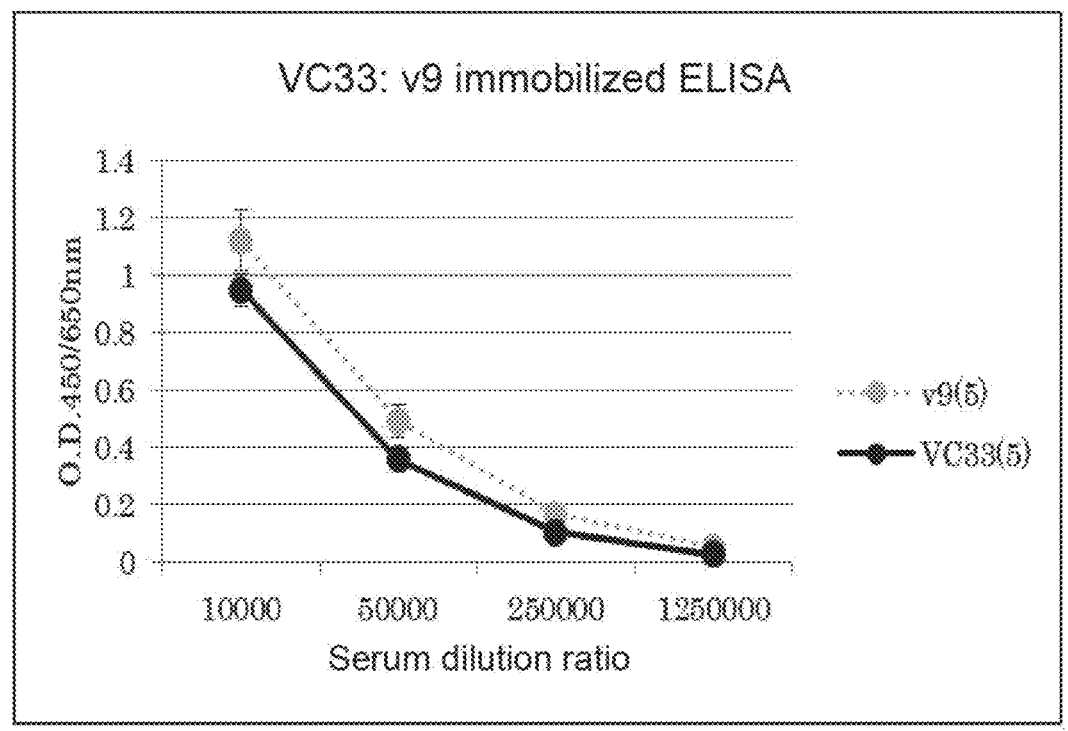
FIG. 2 illustrates a result of immune refocusing from the head region to the body region in Example 6 (VC33).
Figure 2:
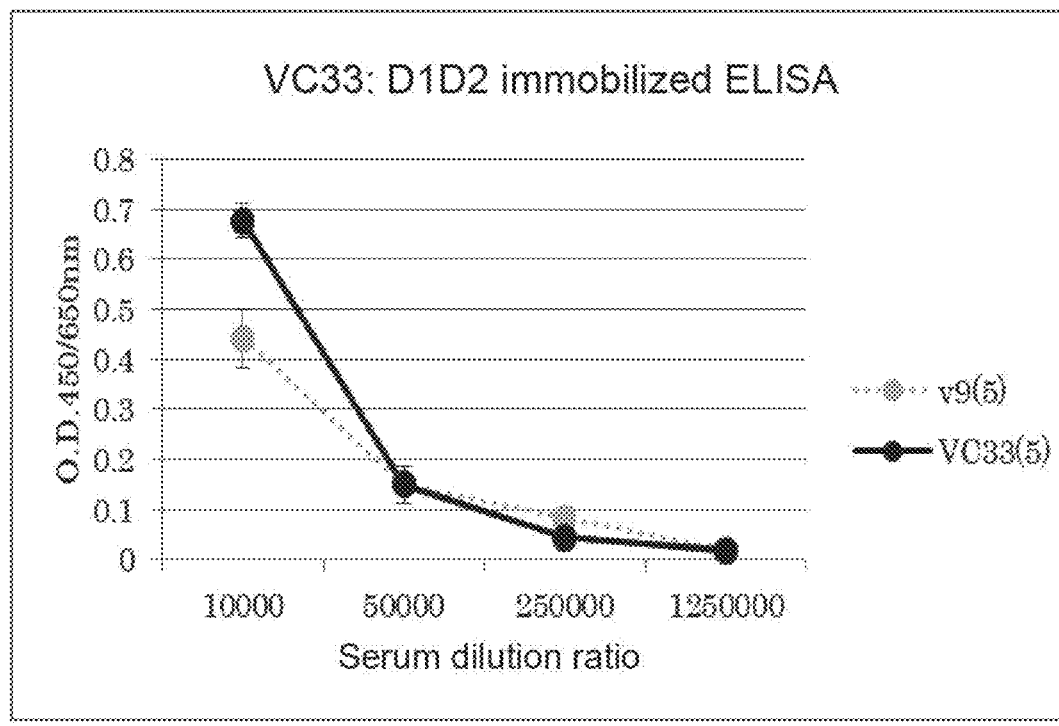
Figure 3:
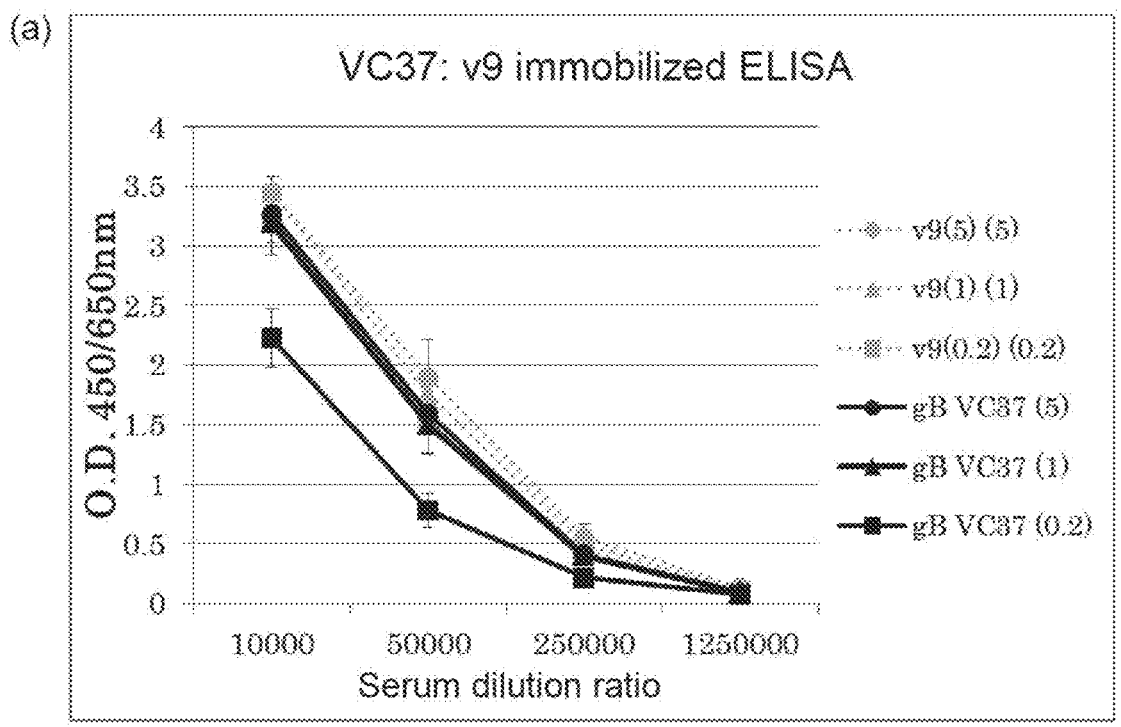
FIG. 3 illustrates a result of immune refocusing from the head region to the body region in Example 6 (VC37).
Figure 3:
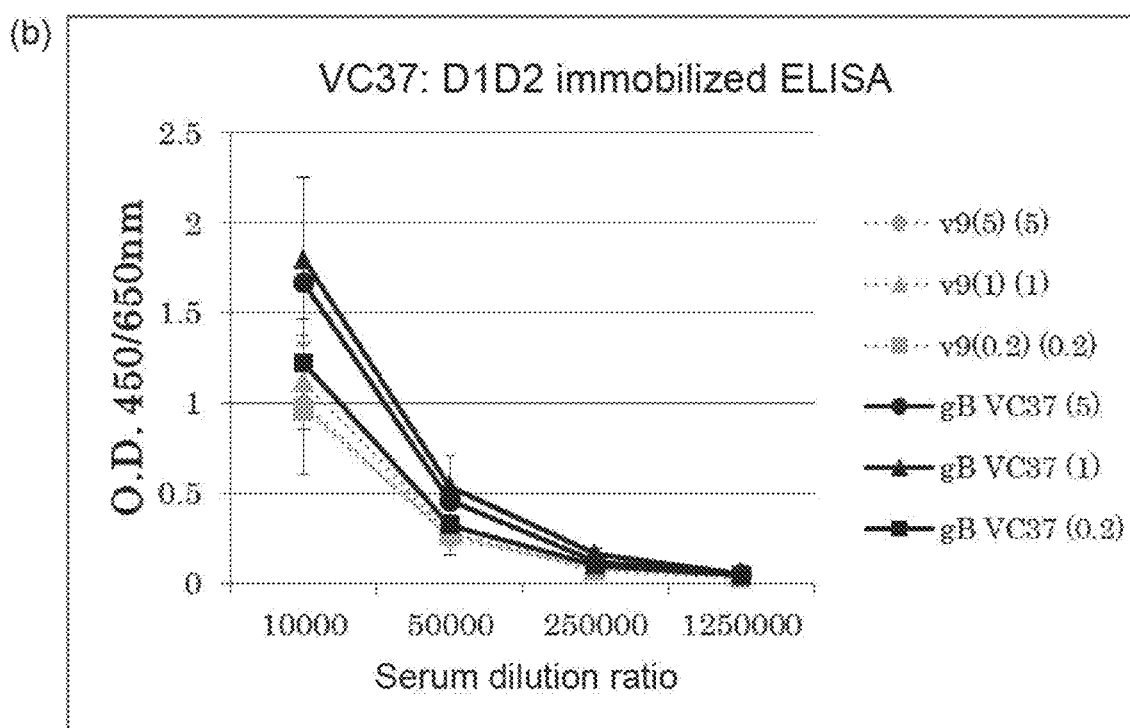
Figure 4:
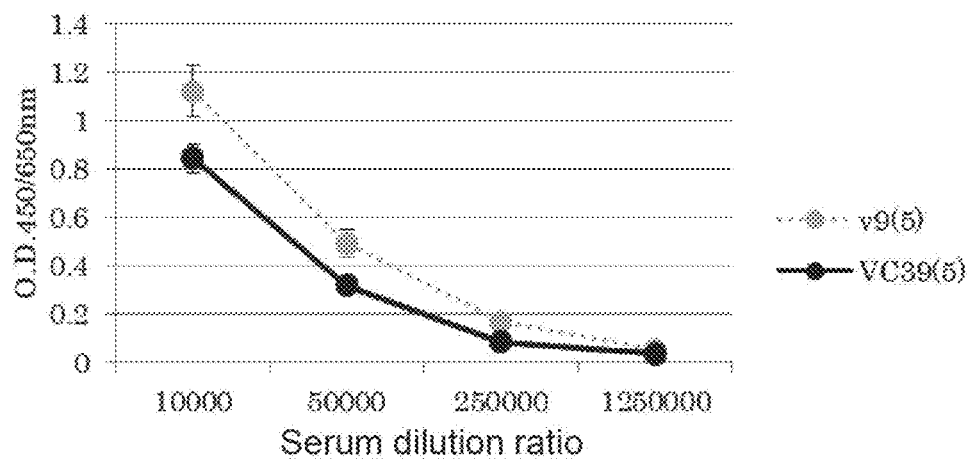
FIG. 4 illustrates a result of immune refocusing from the head region to the body region in Example 6 (VC39).
Figure 4:
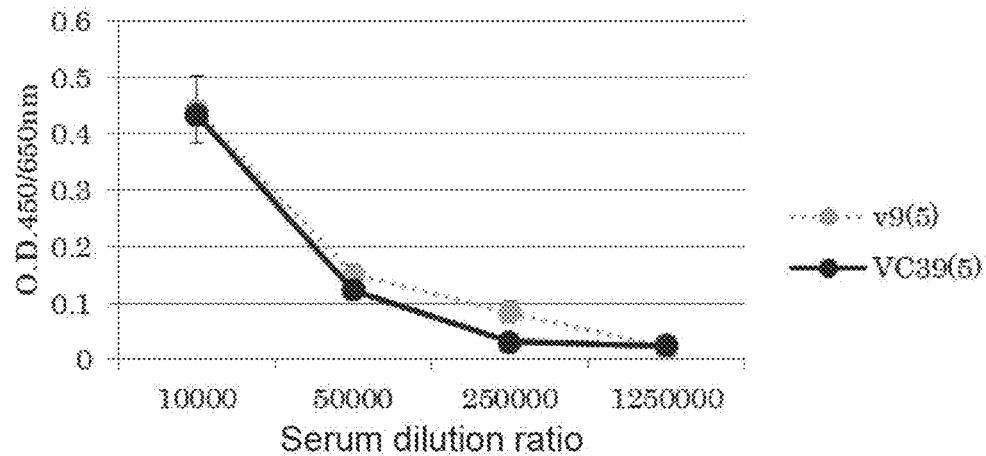
Figure 5:
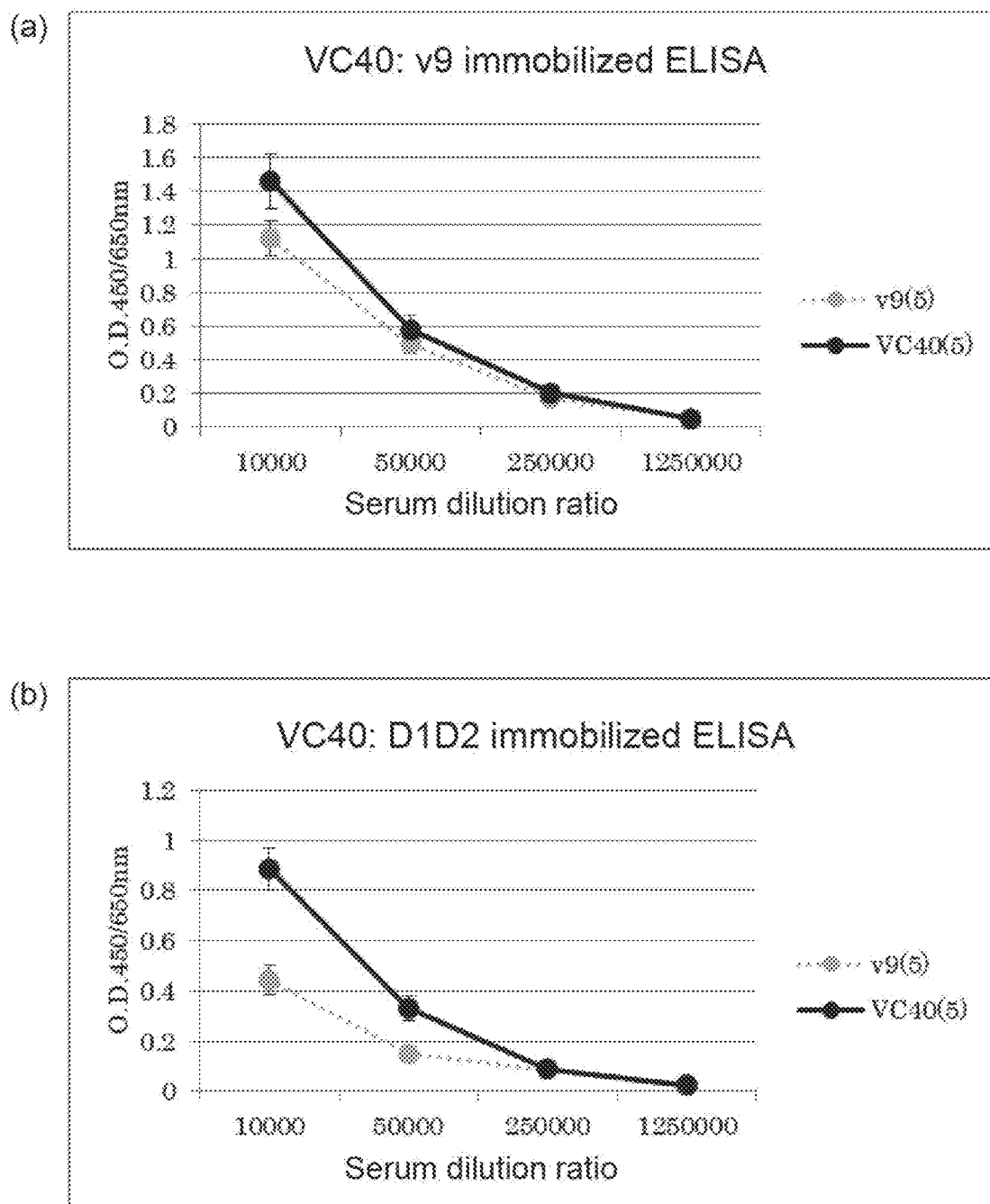
FIG. 5 illustrates a result of immune refocusing from the head region to the body region in Example 6 (VC40).
Figure 6:
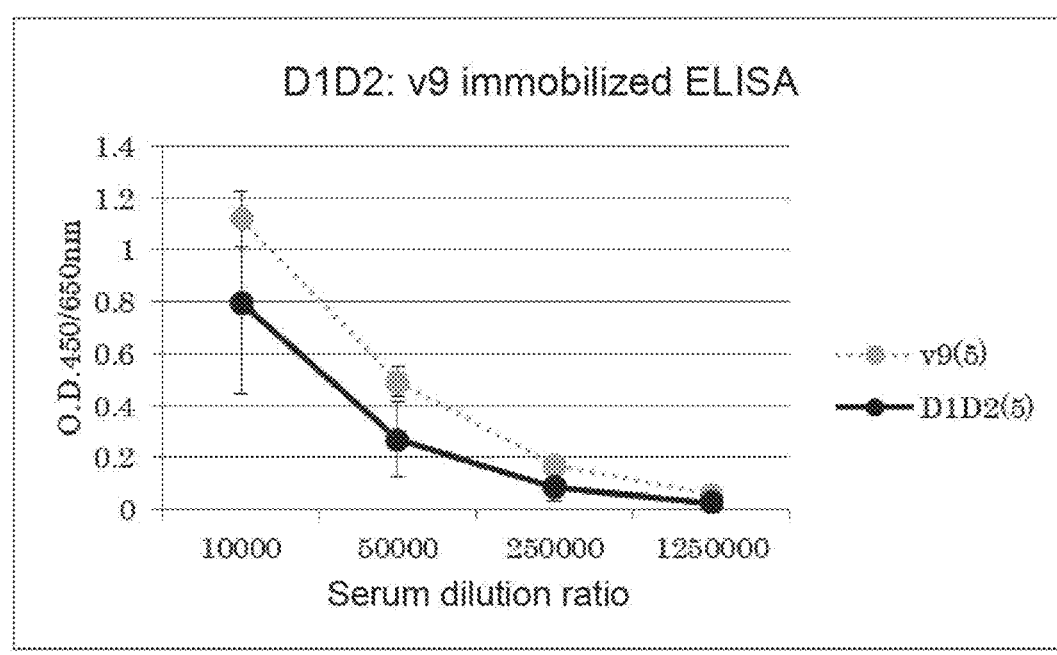
FIG. 6 illustrates a result of immune refocusing from the head region to the body region in Example 6 (D1D2).
Figure 6:
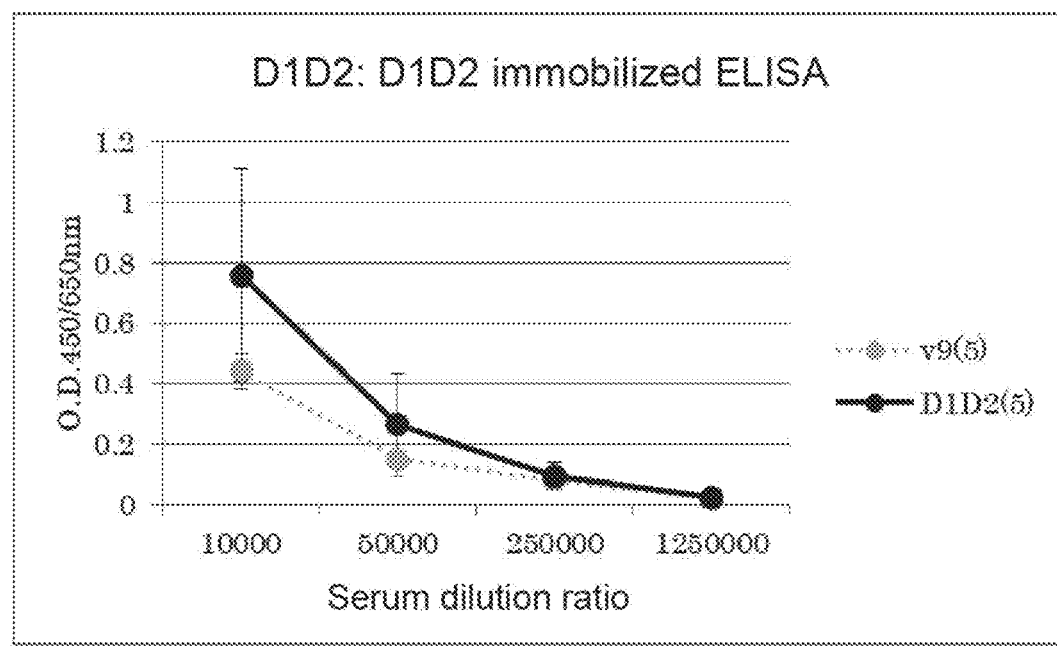
Figure 7:
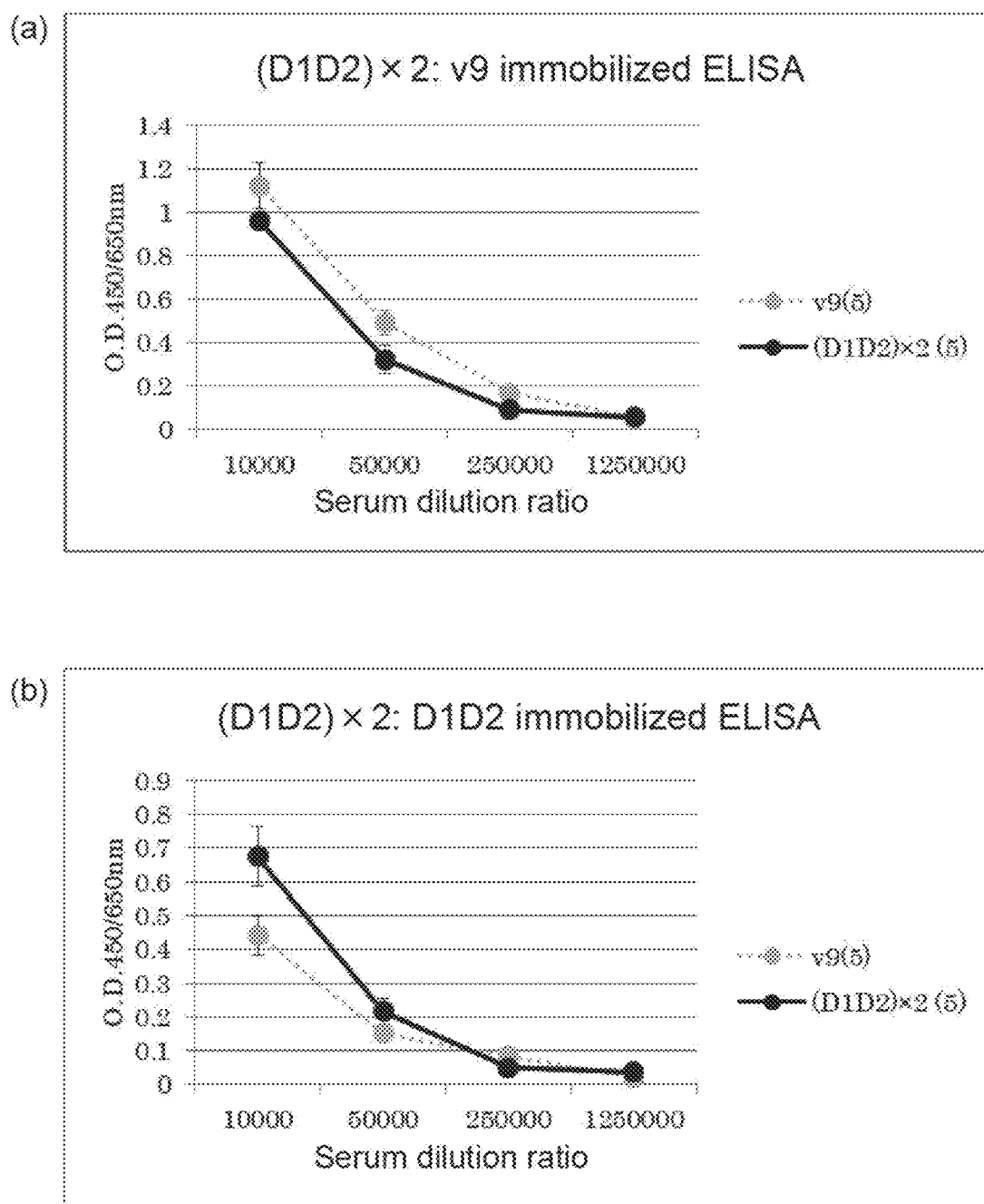
FIG. 7 illustrates a result of immune refocusing from the head region to the body region in Example 6 ((D1D2)×2).

Embodiments of the present invention will be described in detail below. However, the present invention is not limited to the following embodiments.

The modified protein in an envelope glycoprotein B (gB protein) in cytomegalovirus (CMV) according to the present invention is a modified CMV gB protein comprising a head region modified from a head region of a wild type CMV gB protein and having an improved ability to induce antibodies that recognize a body region in the gB protein.

The "wild type CMV gB" means a gB protein derived from any CMV strain and examples thereof include a gB protein (GenBank ACCESSION No.: X17403.1, SEQ ID NO: 1) derived from the strain CMV AD169 having the amino acid sequence set forth in SEQ ID NO: 1. To facilitate understanding, the numbering for positions of amino acid residues herein is described, unless when otherwise stated, in relation to the amino acid sequence of the gB protein derived from the strain AD169 and set forth in SEQ ID NO: 1 without a leader sequence. In this case, positions of amino acid residues in a gB protein are expressed as their corresponding positions in the amino acid sequence set forth in SEQ ID NO: 1 based on sequence alignment, that is, "corresponding positions".

The "modified CMV gB proteins" (also referred to as "gB variants" or "variants") refers to proteins modified from the wild type CMV gB by substitution, deletion, or addition of at least one amino acid residue or region of consecutive amino acid residues and also include proteins with a protein modification not found in wild type proteins, such as proteins with sugar chain introduction by substitution or deletion of an amino acid residue.

The conformation of the CMV gB protein is analyzed (Non Patent Literature 8) and, for example, it is known for gB derived from the strain AD169 to have Domain I having the amino acid residues at positions 109-319; Domain II having the amino acid residues at positions 97-108 and the amino acid residues at positions 320-414; Domain III having the amino acid residues at positions 71-87, the amino acid residues at positions 453-525, and the amino acid residues at positions 614-643; Domain IV having the amino acid residues at positions 65-70 and the amino acid residues at positions 526-613; and Domain V having the amino acid residues at positions 644-675 in SEQ ID NO: 1.

The domain structure of CMV gB has been reported in Non-Patent Literature 7. In CMV gB proteins, a region containing Domain IV is referred to as a head region, which is, for example, the region consisting of the amino acid residues at positions 1-87 and 415-649 in the CMV gB protein derived from the strain AD169. The remaining ectodomain region containing mainly Domain I and Domain II is referred to as a body region, which is, for example, a region consisting of the amino acid residues at positions 88-414 and the amino acid residues at positions 650-682 in the CMV gB protein derived from the strain AD169. Head regions and body regions in other CMV gB proteins may be identified with amino acid residues at corresponding positions to the positions in the CMV gB protein derived from the strain AD169.

As for the crystal structure of the CMV gB protein, it is known that the head region has higher probability of causing antigen presentation than the body region does and, in other words, the head region induces more antibodies in comparison to the body region. However, epitopes present in Domain IV induce many antibodies with no or low neutralizing activity. It has been reported that, as a result, Domain IV in the gB protein serves as an immune evasion mechanism for CMV (Non Patent Literature 7, 8).

Actually, in the investigation of the present inventors, the proportion of antibodies to the head region in the antibodies in blood also is higher than the proportion of antibodies to the body region. Meanwhile, the head region in the wild type CMV gB induced nonneutralizing antibodies with no or low neutralizing activity more than neutralizing antibodies with high neutralizing activity, according to the study of the present inventors. Therefore, it was concluded that there are more nonneutralizing epitopes, which induce nonneutralizing antibodies, than neutralizing epitopes, which induce neutralizing antibodies present in the head region. Nonneutralizing antibodies bind to the virus, but cannot suppress infectivity of the virus. Therefore, the ability to induce production of neutralizing antibodies is considered to be important in designing a vaccine antigen.

In the modified CMV gB protein according to the present invention, Domain I and Domain II, which are the body region, whose neutralizing antibody-inducing ability is higher than the head region, are made outstanding by modifying the head region in the gB protein, in which many nonneutralizing epitopes are considered to be present. As a result, the modified CMV gB protein according to the present invention has an improved ability to induce body region-recognizing antibodies and is capable of increasing the amounts of antibodies induced by epitopes present in Domain I and Domain II which are the body region, and the modified CMV gB protein according to the present invention can induce more neutralizing antibodies in comparison to the wild type CMV gB protein.

The "ability to induce body region-recognizing antibodies" or "activity of inducing body region-recognizing antibodies" refers to ability or activity to induce the production of antibodies that recognize epitopes present in the body region. The "neutralizing antibody inducing ability" or "activity to induce neutralizing antibodies" refers to ability capable of inducing neutralizing antibodies to an antigen protein, which can be evaluated with the neutralizing antibody titer in immune serum obtained by inoculating the antigen protein into a test animal. The "neutralizing antibody" refers to an antibody capable of eliminating the infectivity of virions and the level of the neutralizing activity of the antibody can be evaluated with the concentration (NT50) of the antibody necessary to decrease, for example, 50% of the number of plaques of the test virus.

As an example of the modified CMV gB protein, the ability to induce antibodies that recognize the body region in the gB protein may be improved by applying modification that makes a sugar chain introduction (glycosylation) in the head region. Furthermore, as the glycosylation in the head region, glycosylation may be made at 2 positions. More preferably, glycosylation may be made at 3 positions in the head region. Further preferably, glycosylation may be made at 4 positions or glycosylation may be made at 5 or more positions in the head region.

In the modified CMV gB protein, modification applying glycosylation to at least 2 positions or at least 3 positions selected from amino acid residues at corresponding positions to the positions 77, 544, 588, and 609 in the amino acid sequence set forth in SEQ ID NO: 1 may be made. It is preferable that it is modification that applies glycosylation to amino acid residues at corresponding positions to the positions 77, 544, and 588 in the amino acid sequence set forth in SEQ ID NO: 1 or a modification that adds glycosylation to amino acid residues at corresponding positions to the positions 77, 544, 588, and 609 in the amino acid sequence set forth in SEQ ID NO: 1. Here, applying glycosylation to amino acid residues include mutating the amino acid residues at the target sites for the sugar chain introductions into other amino acid residues appropriate to introduce sugar chains.

The method of glycosylation may be a conventional method and is not particularly limited, but, for example, when a N-sugar chain is introduced, a cDNA of the wild type gB protein is used as a template, primers are designed such that the 3 consecutive amino acid sequences at the target site to introduce the N-sugar chain are N-X-S/T (X is any amino acid other than proline), and a mutation is introduced by PCR. Examples of the mutation for sugar chain introductions include the following mutations in the amino acid sequence set forth in SEQ ID NO: 1: (D77N, I79T), (E544N, P546T), (L588N, P589G), and (K609N, R610T, M611T). A modified CMV gB protein can be obtained by cloning a nucleic acid sequence for the modified gB protein of interest or the nucleic acid sequence further linked to a tag such as 6×His, as needed, into an appropriate vector and expressing the nucleic acid sequence. Then, an N-sugar chain is added to asparagine of the target site of the gB variant by a usual method.

It is preferable that the sugar chain introduction be made according to the following. By sugar chain introductions at these positions, epitopes in the head region are modified (deimmunized) and modified CMV gB proteins in which epitopes in the body region are made outstanding can be obtained. It is considered that such modified CMV gB proteins can induce more neutralizing antibodies with high neutralizing activity than the wild type CMV gB does.

substitution of an amino acid residue at a corresponding position to the position 77 in the amino acid sequence set forth in SEQ ID NO: 1 with an asparagine residue and substitution of an amino acid residue at a corresponding position to the position 79 in the amino acid sequence set forth in SEQ ID NO: 1 with a threonine residue, and/or substitution of an amino acid residue at a corresponding position to the position 544 in the amino acid sequence set forth in SEQ ID NO: 1 with an asparagine residue and substitution of an amino acid residue at a corresponding position to the position 546 with a threonine residue in the amino acid sequence set forth in SEQ ID NO: 1, and/or substitution of an amino acid residue at a corresponding position to the position 588 in the amino acid sequence set forth in SEQ ID NO: 1 with an asparagine residue and substitution of an amino acid residue at a corresponding position to the position 589 with a glycine residue in the amino acid sequence set forth in SEQ ID NO: 1, and/or substitution of an amino acid residue at a corresponding position to the position 609 in the amino acid sequence set forth in SEQ ID NO: 1 with an asparagine residue, substitution of an amino acid residue at a corresponding position to the position 610 with a threonine residue, and substitution of an amino acid residue at a corresponding position to the position 611 with a threonine residue in the amino acid sequence set forth in SEQ ID NO: 1.

As an example of the modified CMV gB protein, the ability to induce antibodies that recognize the body region in the gB protein may be improved by applying modification that deletes at least part of the head region. An entire region of the head region may be deleted. By deletion of at least part of the head region, epitopes in the head region can be deimmunized to obtain a modified CMV gB protein in which epitopes in the body region are made outstanding. It is considered that such modified CMV gB proteins can induce more neutralizing antibodies with high neutralizing activity than the wild type CMV gB does.

An example of the modified CMV gB protein may contain substitution of an amino acid residue corresponding to the isoleucine residue at the position 132 (I132) in the amino acid sequence set forth in SEQ ID NO: 1 as modification in the body region. Preferably, examples include substitution of the isoleucine at the position 132 with histidine.

An example of the modified CMV gB protein may contain substitution of an amino acid residue corresponding to the tyrosine residue at the position 133 (Y133) in the amino acid sequence set forth in SEQ ID NO: 1 as modification in the body region. Preferably, examples include substitution of the tyrosine at the position 133 with arginine.

An example of the modified CMV gB protein may contain substitution of an amino acid residue corresponding to the tryptophan residue at the position 216 (W216) in the amino acid sequence set forth in SEQ ID NO: 1 as modification in the body region. Preferably, examples include substitution of the tryptophan at the position 216 to alanine.

An example of the modified CMV gB protein may contain substitution of an amino acid residue corresponding to the arginine residue at the position 432 (R432) in the amino acid sequence set forth in SEQ ID NO: 1 as modification in the head region. Preferably, examples include substitution of the arginine at the position 432 to threonine.

An example of the modified CMV gB protein may contain substitution of an amino acid residue corresponding to the arginine residue at the position 434 (R434) in the amino acid sequence set forth in SEQ ID NO: 1 as modification in the head region. Preferably, examples include substitution of the arginine at the position 434 to glutamine.

An example of the modified CMV gB protein may contain substitution of at least one amino acid residue selected from the group consisting of amino acid residues corresponding to I132, Y133, W216, R432, and R434 in the amino acid sequence set forth in SEQ ID NO: 1. Preferably, the example may contain substitution of amino acid residues at 2 positions corresponding to R432 and R434 in the head region. Further preferably, the example may contain substitution of all the amino acid residues corresponding to the 5 positions I132, Y133, W216, R432, and R434. Here, substitution of amino acid residues may be substitution with any other amino acid residue and it is considered that modified CMV gB proteins obtained by the substitution can induce more neutralizing antibodies with high neutralizing activity than the wild type CMV gB does.

An example of the modified CMV gB protein may contain substitution of an amino acid residue corresponding to the threonine residue at the position 215 (T215) in the amino acid sequence set forth in SEQ ID NO: 1 as modification in the body region. Preferably, examples include substitution of the threonine at the position 215 to glutamic acid. In addition to T215, the example may further contain substitution at 5 positions of amino acid residues corresponding to I132, Y133, W216, R432, and R434.

An example of the modified CMV gB protein may contain modification of amino acid residues in Fusion Loop 1 (FL1) domain defined by the amino acids Y-I-Y at positions corresponding (corresponding positions) to the positions from 131 to 133 in the amino acid sequence set forth in SEQ ID NO: 1 or Fusion Loop 2 (FL2) domain defined by the amino acids W-L-Y at positions corresponding to the positions from 216 to 218 in the amino acid sequence set forth in SEQ ID NO: 1.

Here, the modification of an amino acid residue may be deletion, substitution, or addition of or a sugar chain introduction to the amino acid residue. Moreover, modification may be made to an amino acid residue in FL1, but no modification may be made to amino acid residue in FL2. Moreover, modification may be made to an amino acid residue in FL2, but no modification may be made to amino acid residue in FL1. Preferably, examples include modifying amino acid residues in both FL1 and FL2.

As an example of the modification of amino acid residues in FL1 and FL2, all the amino acid residues corresponding to the positions from 131 to 133 in the amino acid sequence set forth in SEQ ID NO: 1 may be deleted. Moreover, all the amino acid residues corresponding to the positions from 216 to 218 in the amino acid sequence set forth in SEQ ID NO: 1 may be deleted. Further preferably, amino acid residues corresponding to the positions from 128 to 138 in the amino acid sequence set forth in SEQ ID NO: 1 may be deleted.

As an example of the modified CMV gB protein, the modified CMV gB protein in which FL1 is deleted may further have an insertion of a linker at the position of the deleted amino acid residues in the amino acid sequence set forth in SEQ ID NO: 1. Preferably, the positions from 128 to 138 in the amino acid sequence set forth in SEQ ID NO: 1 are deleted and a linker may be inserted at the position of the deletion, that is, between the amino acid residues before and after the deleted amino acid residues. Further preferably, a glycine linker may be inserted as the linker.

The modified CMV gB protein according to the present invention may be prepared by a genetic engineering technique. The method of preparation is not particularly limited, but, the modified CMV gB protein according to the present invention may be obtained, for example, by obtaining a nucleic acid having mutation introduced by PCR using a cDNA of the wild type gB protein as a template and designing primers to introduce a mutation of interest, operatively linking the nucleic acid to an expression promoter, optionally further linking a tag, introducing the nucleic acid into an appropriate expression vector, and expressing the nucleic acid. Moreover, in the case of the variant by the sugar chain introduction, it can be obtained as described above.

The prepared modified CMV gB protein may be purified as needed. The method of purification is not particularly limited, but examples thereof include purification with an affinity chromatography column, or the like.

The CMV vaccine according to the present invention comprises a modified CMV gB protein according to the present invention.

The dosage form of the CMV vaccine according to this embodiment may be, for example, liquid form, powdered form (freeze-dried powder, dry powder), tablet form, or frozen state.

The CMV vaccine according to this embodiment may comprise a pharmaceutically acceptable carrier. As the above-described carrier, a carrier that is usually used for vaccine manufacture may be used without limitation and, specifically, examples include saline, buffered saline, dextrose, water, glycerol, aqueous isotonic buffer solutions, and combinations thereof. The vaccine may further contain an emulsifier, a preservative (for example, thimerosal), an isotonizing agent, a pH adjuster, an inactivated agent (for example, formalin), or the like, as appropriate.

To further increase immunogenicity of the CMV vaccine according to this embodiment, an adjuvant may further be contained. Examples of the adjuvant include oil-in-water type emulsion adjuvants (AS03, MF59, and the like) such as aluminum adjuvants or squalene, ligands of Toll-like receptors such as CpG and 3-O-deacyl-4'-monophosphoryl lipid A (MPL), polymer adjuvants such as saponin adjuvants, poly-γ-glutamic acid, and polysaccharides such as chitosan and inulin.

The CMV vaccine according to this embodiment can be obtained by mixing the modified CMV gB protein according to the present invention and a carrier, an adjuvant, or the like, as needed. The adjuvant may be an adjuvant that is mixed at the time of use.

The administration route of the CMV vaccine according to this embodiment may be, for example, transdermal administration, sublingual administration, ophthalmic administration, intradermal administration, intramuscular administration, oral administration, enteral administration, transnasal administration, intravenous administration, subcutaneous administration, intraperitoneal administration, or inhalational administration from mouth to lung.

The mode of administration of the CMV vaccine according to this embodiment may be, for example, a mode of administration with a syringe, a transdermal patch, microneedles, an implantable sustained release device, a syringe with microneedles, a needle-free device, or spray.

EXAMPLES

The present invention will be described more specifically based on the following Examples. However, the present invention is not limited to the following Examples.

Example 1 Preparation of CMV gB Protein and Variants Thereof

The ectodomain (amino acid residues at the positions 1-682 in SEQ ID NO: 1, which may, herein, be referred to as "gB1-682") of CMV gB derived from the strain AD169 was cloned into pCAGGS1-dhfr-neo, which is disclosed in International Publication No. WO 03/004647. It was designed so that His tag, Strep tag II, or FLAG tag was added to the C terminus of gB. On the basis of these, the variants set forth in Table 1 and the variants set forth in Table 2 were prepared.

TABLE 1

| Name of variant | Modification |
|---|---|
| gB1-682-fm | gB1-682 (with R434A, R435A) |
| gB1-682-fm3Mv9 | gB1-682 (with I132H, Y133R, T215E, W216A, R432T, R434Q) |

As set forth in Table 1, "gB1-682-fm" is a variant in which the amino acid residue substitution of R434A and R435A in gB1-682 have been made and "gB1-682-fm3Mv9" is a variant in which the amino acid residue substitution of I132H, Y133R, T215E, W216A, R432T, and R434Q in gB1-682 have been made in reference to Non-Patent Literature 8.

TABLE 2

| No. | Name of variant | Modification |
|---|---|---|
| 1 | gB1-682-fm3M | gB1-682 (with I132H, Y133R, W216A, R432T, R434Q) |
| 2 | gB-D1 | gB109-319 (with I132A, Y133A, W216A) |
| 3 | gB-D2 | gB88-108-IAGSG-gB320-414 |
| 4 | gB-Δd1 | gB1-108-IAGSG-gB320-649 |

As set forth in Table 2, Variant (1) "gB1-682-fm3M" is a variant in which the amino acid residue substitution of I132H, Y133R, W216A, R432T, and R434Q in gB1-682 have been made, Variant (2) "gB-D1" is a variant in which the positions 1-108 and 320-682 in gB1-682 have been deleted and the amino acid residue substitution of I132A, Y133A, and W216A have been made, Variant (3) "gB-D2" is a variant in which a deletion variant in which the positions 1-87 and 109-682 in gB1-682 have been deleted and a deletion variant in which the positions 1-319 and 415-682 in gB1-682 have been deleted were connected with the 5 amino acid residues IAGSG, and Variant (4) "gB-Δd1" is a variant in which a deletion variant in which the positions 109-682 in gB1-682 have been deleted and a deletion variant in which the positions 1-319 and 650-682 in gB1-682 have been deleted were connected with the 5 amino acid residues IAGSG.

For the expression of each of the variants, FreeStyle 293 or Expi293 expression systems (Life Technology Inc.) were used. The expression plasmid was transfected into cells and culture supernatant was collected in 4 to 6 days. The culture supernatant containing a gB variant which His tag was added to was subjected to purification using Ni-NTA Agarose (QIAGEN N.V. Cat. 30230) to obtain a purified gB variant. The culture supernatant containing a gB variant which Strep Tag II was added to was subjected to buffer substitution to PBS and concentration with a UF membrane (Ultracel YM-3/Millipore Cat. 4303 or Centriprep-10 K/Millipore Cat. 4305) to remove Biotin contained in the medium. The concentrated culture supernatant was subjected to purification using a StrepTactin column to obtain a purified gB variant. The culture supernatant containing a gB variant which FLAG tag was added to was subjected to purification using Anti-FLAG M2 Agarose Affinity gel (SIGMA-ALDRICH Corporation Cat. A2220) to obtain a purified gB variant.

Example 2 Preparation of Anti-gB Antibodies

By screening the phage display library (XOMA020) containing $10^{11}$ or more kinds of various scFv molecules prepared from mRNA derived from human B cells (for example, lymph node or spleen) using cDNAs of human VH and VL, antibodies against the variants were isolated. As a method of screening, a standard technique of immobilized antigen panning was used (Antibody Phage Display Methods and Protocols, Edited by Philippa M. O'Brien and Robert Aitken).

Specifically, gB antigens were immobilized onto 96 well plates, the phage display library containing the scFv molecules was allowed to react with them, and after washing, elution with an alkaline solution was conducted. The phages containing the scFv molecules were rescued using the

*Escherichia coli* strain TG1 and M13KO7 Helper Phage. This cycle was repeated 2-3 rounds to concentrate and isolate gB antigen-specific phage clones.

When conducting subtraction in panning, the following technique was used. The gB antigens were immobilized onto 96 well plates and, when allowing the phage display library containing the scFv molecules to react with them, the following scFv-hFcs of 1-3-13, 6-2-8, and 8-2-2 were allowed to coexist. The washing and later steps were conducted in the same way as the aforementioned panning As a result of the screening, 65 kinds of clones were obtained. The obtained clones were named "J9", "J19", "J25", "J47", "J58", "J61", "J82", "J92", "K12", "K17", "K29", "K42", "K61", "K74", "K90", "K91", "M33", "N66", "N79", "N80", "N93", "P12", "P30", "P40", "P86", "Q5", "Q12", "Q25", "Q38", "Q41" "Q44", "Q62", "Q92", "R18", "R23", "R40", "R47", "R57", "R87", "S68", "S80", "1-3-13", "2-3-4", "2-3-42", "2-3-77", "3-3-15", "3-3-88", "6-2-5", "6-2-8", "6-2-18", "6-2-98", "6-2-146", "6-3-106", "7-2-25", "7-2-36", "7-2-58", "7-2-64", "7-2-66", "7-3-38", "7-3-45", "8-2-2", "8-2-12", "8-2-16", "8-2-72", and "8-2-82".

<Method of Preparing scFv-Fc>

The variable regions of the isolated scFv genes were linked to an Fc gene (CH2-CH3) derived from human IgG1 and cloned into pCAGGS1-dhfr-neo vector prepared in reference to International Publication No. WO 2015/115331 to construct an scFv-hFc expression plasmid. For expression, FreeStyle293 or Expi293 expression system (Life Technology Inc.) was used. The expression plasmid was transfected into cells and culture supernatant was collected in 4 to 6 days. The culture supernatant was purified using Ab-Rapid PuRe 10 (ProteNova Cat. P-012-10) or Ab-Rapid PuRe Ex (ProteNova Cat. P-015-10) to obtain scFv-hFc.

<Method of Preparing Human IgG>

Next, the VH regions of the isolated scFv genes were linked to an H chain constant region gene (CH1-CH2-CH3) derived from human IgG1 and cloned into the pKMA010-hCg1 vector prepared in reference to International Publication No. WO 2015/115331 to construct an H chain expression plasmid. Moreover, a VL region was linked to a human CL gene and cloned into the pKMA009-hCL vector prepared in reference to International Publication No. WO 2015/115331 to construct an L chain expression plasmid. For expression, FreeStyle293 or Expi293 expression system (Life Technology Inc.) was used. The expression plasmid was transfected into cells and culture supernatant was collected in 4 to 6 days. Culture supernatant was purified using a Hi-Trap Protein A HP Column (GE Healthcare Cat. 17040303) to obtain human IgG.

<Method of Preparing scFv Phage>

The *Escherichia coli* strain TG1 having the phagemid vectors in which the isolated scFv genes were cloned was cultured in 2×YTCG medium (37° C.) and infected with M13K07 helper phage at an moi=20, and then the phages were expressed in 2×YTCK medium (25° C.), overnight. The obtained scFv phages were subjected to concentration with 20%-PEG-2.5 M NaCl.

Example 3 Reactivity Analysis and Grouping of gB Antibody

<Grouping by Binding Activity of scFv Phage to Each of the Variants>

The binding activity of the scFv phages obtained in Example 2 was evaluated by ELISA using the variants set forth in Table 2 in Example 1. Each variant was diluted to 1 µg/mL with PBS (SIGMA) and each variant was immobilized by transferring 100 µL into a MaxiScorp plate (Nunc) and incubating at 4° C. overnight or at room temperature for 1-2 hours.

After the immobilization, the plate was washed with PBS and 100 µL of the obtained scFv phages were added into a well in the plate, which was incubated for 1 hour at room temperature. Subsequently, it was washed with PBS-0.05% Tween 20 (PBST) and then 100 µL of the detection antibody Anti-M13/HRP (GE Healthcare Cat. 27-9421-01) was added to the well in the plate, which was incubated for 1 hour at room temperature. Subsequently, color development was performed by washing with PBST and adding 100 µL of TMB (SIGMA Cat. T-4444) to the well in the plate. 30 minutes later, the reaction was stopped with 1 N sulfuric acid and the color value (O.D. 450 nm/650 nm) was measured with a microplate reader (Molecular Devices, LLC).

Based on the difference in reactivity between the obtained 65 clones of antibodies and the variants prepared in Example 1, the recognition regions of each of the antibodies were determined. As the variants, Variant (1) gB1-682-fm3M, Variant (2) gB-D1, Variant (3) gB-D2, and Variant (4) gB-Δd1 set forth in Table 2 in Example 1 were used.

Based on the reactivity of each of the variants, the obtained 65 clones of antibodies were classified and those having reactivity with Variant (2) or (3) and those having reactivity with Variant (1), but not having reactivity with Variant (4) classified as body region-recognizing antibodies, and those having reactivity with Variant (1) but are not the aforementioned body region-recognizing antibodies were classified as head region-recognizing antibodies.

As a result, the 65 clones were classified into 21 clones of body region-recognizing antibodies and 44 clones of head region recognizing antibodies. From this result, it was found that epitopes in the obtained 65 clones of antibodies were converged in the head region.

<Grouping by Competition ELISA Between scFv Phage and scFv-Fc>

The 65 clones of antibodies were classified by competition ELISA between scFv phages and scFv-Fc obtained in Example 2. The variant gB1-682 fm3Mv9 set forth in Table 1 was diluted to 1 µg/mL with PBS (SIGMA) and the variant was immobilized by transferring 100 µL into a MaxiSorp plate (Nunc) and incubating at 4° C. overnight. After the immobilization, the plate was washed with PBS and 50 µL of the obtained scFv-Fc was added into a well in the plate, which was incubated for 1 hour at room temperature. Subsequently, the plate was washed with PBST and 100 µL of the detection antibody anti-M13/HRP (GE Healthcare Cat. 27-9421-01) was added to the well in the plate, which was incubated for 1 hour at room temperature. Subsequently, color development was performed by washing with PBST and then adding 100 µL of TMB (SIGMA Cat. T-4444) to the well in the plate. 30 minutes later, the reaction was stopped with 1 N sulfuric acid and the color value (O.D. 450 nm/650 nm) was measured with a microplate reader (Molecular Devices, LLC).

From reactivity tendencies of each of the antibodies, the body region was subdivided into seven groups and the head region was subdivided into 13 groups, as set forth in Table 3.

TABLE 3

Grouping of body region-recognizing antibody and head region-recognizing antibody

| Body region | Group 1 | P12, Q12, Q38, Q44, 3-3-15, 7-2-58, 7-3-45, 8-2-16 |
|---|---|---|
| | Group 2 | Q25, Q41, Q62, 3-3-88, 7-2-64, 7-3-38 |
| | Group 3 | N80, Q5, 7-2-36 |
| | Group 4 | S68 |
| | Group 5 | 7-2-66 |
| | Group 6 | 8-2-12 |
| | Group 7 | N79 |
| Head region | Group 1 | J9, R23, R40, 2-3-77, 6-2-98, 6-3-106 |
| | Group 2 | K29, S80, 6-2-5 |
| | Group 3 | J92, K74, 1-3-13, J25, K42, K91, R87, K12, 6-2-8, 8-2-2, 8-2-82 |
| | Group 4 | M33, 2-3-4 |
| | Group 5 | R18, R57, 6-2-18, 7-2-25, 8-2-72 |
| | Group 6 | J19, R47 |
| | Group 7 | J47, P40, P86, P30, 2-3-42, Q92 |
| | Group 8 | K17, K90 |
| | Group 9 | J82, N66 |
| | Group 10 | J61, 6-2-146 |
| | Group 11 | K61 |
| | Group 12 | J58 |
| | Group 13 | N93 |

Example 4 Neutralization Test of Each of the Antibodies

[Preparation of Cells and Viruses]

<Preparation of Cells of Fibroblast Cell Line and Viruses>

For the culture of virus, the neutralization test, and the analysis of ability to induce neutralizing antibodies with the fibroblast cell line, MRC-5 cells (CCL.171) purchased from ATCC were used. The medium for cell culturing was prepared by adding 2 mM L-glutamine, 1 mM sodium pyruvate, and non-essential amino acids (10 mM each of Glycine, L-Alanine, L-Asparagine, L-Aspartic acid, L-Glutamic Acid, L-Proline, and L-Serine) to MEM medium. The medium containing 10% FBS was used at the time of expansion, maintenance, and preparation of analytic plates and the medium containing 2% FBS was used at the time of the evaluation of ability to induce neutralizing antibodies and culturing was performed under conditions at 37° C. and 5% $CO_2$ concentration for them all.

The human herpesvirus 5 (CMV) strain AD169 (VR-538) purchased from ATCC was used as the virus for the neutralization test and the analysis of ability to induce neutralizing antibodies with the fibroblast cell line. Full sheets of MRC-5 cells were inoculated with the virus at an moi=0.1-1, then cultured in the medium containing 2% FBS for 4-11 days, and subjected to three times of freeze-thawing and then centrifugation at 2150 g was conducted at room temperature for 10 minutes to obtain supernatant as a virus bank for the analysis of neutralizing antibody titer using fibroblast cells.

<Preparation of Cells of Epithelium Cell Line and Viruses>

For the culture of virus, the neutralization test, and the analysis of ability to induce neutralizing antibodies with the epithelium cell line, APRE-19 cells (CRL2302) purchased from ATCC were used. The human epithelium cell ARPE-19 was subcultured at 1:5 using the F12/DMEM medium containing 10% FBS (Fisher Scientific).

As a virus to be used for the neutralization test and the analysis of ability to induce neutralizing antibodies with the epithelium cell line, the strain AD169rev capable of proliferating with APRE-19 cells was established by infecting APRE-19 cells with the strain AD169 (VR-538) and sub-culturing infected cells with noninfected cells at a ratio of 1:4 to 1:10 for a long period of time. Cells infected with the strain CMV AD169rev presenting 50% CPE were adjusted to an moi of 0.1 with the medium containing 10% FBS, and this was inoculated into an about 80% full sheet of ARPE-19 cells. This was cultured for one week after the inoculation and the culture liquid was collected and centrifugation at 1800 g was conducted at room temperature for 10 minutes to obtain supernatant as a virus bank ($5\text{-}10\times10^4$ PFU/mL) for analysis of neutralizing antibody titer with epithelium cells. While it has been reported that the strain AD169 subcultured with fibroblast cells has a frameshift mutation in UL131A and pentamer is not formed, it was confirmed by nucleotide sequence analysis that this mutation has been restored to the wild type in the strain AD169rev.

[Neutralization Test]

<Neutralization Test of Each of the Antibodies in Fibroblast Cell Line>

The analysis of neutralizing antibody titer using fibroblast cells was conducted using the activity of reducing the number of foci (focus reduction activity). For the analysis, plates obtained by culturing overnight MRC-5 cells seeded onto 96 black wall well plates (Corning 3340) processed with CellBIND or sell carrier-96 Ultra Collagen coated plates (PerkinElmer 6055700) at $2\times10^4$ cells/well were used.

Each monoclonal antibody was serially diluted to adjust the concentration to a predetermined concentration and mixed with the strain CMV AD169 at about 100-1000 PFU and then reacted at 37° C. for one hour. Cells in the analytic plates were inoculated with the reaction solution at 30 μL/well and then centrifugation at 400 g was conducted at room temperature for 30 minutes and the virus was adsorbed onto the cells. The reaction solution was removed and washing with an FBS free medium was conducted once and then culturing in the medium containing 2% FBS was conducted for 16-20 hours. After the culture, inactivation and fixation of cells with 50% acetone/PBS were performed at room temperature for 20 minutes. Subsequently, this was treated at room temperature with 0.1% Triton-X100 for 10 minutes and, after washing, a 1 μg/mL anti-CMV IE1-IE2 monoclonal antibody (CH160:Abcam ab53495, Santacruz sc-69748) was reacted at 37° C. for one hour. After washing, 1 μg/mL Goat Anti-Rabbit IgG H & L (Alexa Fluor® 488) (Abcam ab150077) was reacted at 37° C. for one hour, and after further washing, 1 μg/mL—Cellstain®—Hoechst 33342 solution (dojindo 346-07951) was reacted at room temperature for 10 minutes and PBS containing 0.5% BSA was added to a washed plate at 100 μL/well; images of each of the wells were taken in with ImageXpress micro (Molecular Devices); the number of cells that reacted with the CMV IE1-IE2 monoclonal antibody and the total number of cells were counted using the analytic software MetaXpress (Molecular Devices) and the proportion of the number of cells that reacted with the CMV IE1-IE2 monoclonal antibody to the total number of cells was calculated. Based on the proportion of the number of cells that reacted with the CMV IE1-IE2 monoclonal antibody when only the virus was added, the neutralizing activity was determined from the suppression rate of the proportion of the number of cells with each immune serum.

<Neutralization Test of Each gB Antibody in Epithelium Cell Line>

The analysis of neutralizing antibody titer of each antibody using epithelium cells was conducted using the activity of reducing the number of foci (focus reduction activity). For the analysis, plates obtained by culturing overnight ARPE-19 cells seeded onto 24 well plates (Corning 3526) at 7×10⁴ cells/well were used. Test substances were serially diluted to adjust the concentrations to predetermined concentrations and mixed with about 200 PFU of the strain AD169rev and a total amount of 25 µL was reacted at 37° C. for 30 minutes. After inoculating cells on the analytic plates with 20 µL of the reaction solution, the plates were left to stand at 37° C. for two hours and the virus was adsorbed onto the cells. The reaction solution was removed and culturing in the medium containing 10% FBS was conducted for 5 days. After culturing, inactivation and fixation of cells with 3.7% formalin/PBS were performed at room temperature for 5 minutes. After washing with PBS at room temperature three times at 5-minute intervals, treatment with 0.5% Triton-X100/PBS was performed for 10 minutes and after washing with PBS, 2 µg/mL of the anti-CMV IE1/IE2 monoclonal antibody (MAb810, Millipore) was reacted at 37° C. for 1 hour. After washing, 100 µL/well of the peroxidase-labeled anti-mouse IgG (N-Histofine Simple Stain MAXPO, Nichirei) was reacted at 37° C. for 1 hour and a color reaction using the DAB substrate (Roche) was finally performed; after washing with water and drying, the number of foci immunostained was counted under stereoscopic microscope. Based on the number of foci when only a medium was added instead of a test substance, the neutralizing activity was determined from a suppression rate of the number of foci with the test substances. The results determined are shown in Table 4 (neutralizing activity of body region-recognizing antibodies) and Table 5 (neutralizing activity of head region-recognizing antibodies).

TABLE 4

Neutralizing activity of body region-recognizing antibodies against MRC5 cells and ARPE cells

| Region | Clone | MRC5 | ARPE19 |
|---|---|---|---|
| Body region | P12 | +++ | +++ |
| | Q25 | +++ | +++ |
| | N80 | − | − |
| | Q5 | + | + |
| | S68 | − | N.T. |
| | 7-2-66 | + | − |
| | 8-2-12 | + | + |
| | Q12 | +++ | N.T. |
| | Q38 | +++ | N.T. |
| | Q44 | +++ | N.T. |
| | 3-3-15 | +++ | N.T. |
| | 7-2-58 | +++ | N.T. |
| | 7-3-45 | +++ | N.T. |
| | 8-2-16 | +++ | N.T. |
| | Q41 | +++ | N.T. |
| | Q62 | +++ | N.T. |
| | 3-3-88 | +++ | N.T. |
| | 7-2-64 | +++ | N.T. |
| | 7-3-38 | ++ | N.T. |
| | 7-2-36 | − | N.T. |
| | N79 | +++ | +++ |

N.T.: not tested

TABLE 5

Neutralizing activity of head region-recognizing antibodies against MRC5 cells and ARPE cells

| Region | Clone | MRC5 | ARPE19 |
|---|---|---|---|
| Head region | J9 | − | − |
| | K29 | ± | − |
| | S80 | + | ++ |
| | J92 | ± | + |
| | K74 | − | + |
| | 1-3-13 | + | +++ |

TABLE 5-continued

Neutralizing activity of head region-recognizing antibodies against MRC5 cells and ARPE cells

| Region | Clone | MRC5 | ARPE19 |
|---|---|---|---|
| | M33 | ± | + |
| | 2-3-4 | ++ | ± |
| | R18 | − | − |
| | J19 | + | − |
| | R47 | − | + |
| | J47 | − | − |
| | P40 | ++ | − |
| | Q92 | ± | ± |
| | K17 | − | − |
| | J82 | ± | − |
| | N66 | − | − |
| | J61 | − | − |
| | K61 | − | − |
| | J58 | − | − |
| | N93 | − | +++ |
| | 6-2-146 | − | N.T. |
| | R23 | − | N.T. |
| | R40 | − | N.T. |
| | 2-3-77 | − | N.T. |
| | 6-2-98 | − | N.T. |
| | 3-6-106 | − | N.T. |
| | 6-2-5 | ± | N.T. |
| | J25 | − | N.T. |
| | K42 | − | N.T. |
| | K91 | − | N.T. |
| | R87 | − | N.T. |
| | K12 | − | N.T. |
| | 6-2-8 | − | N.T. |
| | 8-2-2 | − | N.T. |
| | 8-2-82 | − | N.T. |
| | R57 | − | N.T. |
| | 6-2-18 | − | N.T. |
| | 7-2-25 | − | N.T. |
| | 8-2-72 | − | N.T. |
| | P86 | − | N.T. |
| | P30 | − | N.T. |
| | 2-3-42 | + | N.T. |
| | K90 | − | N.T. |

N.T.: not tested

The virus-neutralizing activity in the MRC-5 (fibroblast cell) infection system and the ARPE (epithelium cell) infection system was analyzed at three points of concentrations of 1 µg/mL, 10 µg/mL, and 100 µg/mL and strong neutralizing antibodies at 1 µg/mL or less in virus-neutralizing activity level as expressed by the 50% plaque-reducing concentration (IC50) were evaluated as "+++", moderate neutralizing antibodies at 1-10 µg/mL as "++", weak neutralizing antibodies at 10-100 µg/mL as "+", those having a plaque-reducing rate of less than 50% at 100 µg/mL, but showing a slight neutralizing tendency as "+/−", and nonneutralizing antibodies showing no neutralizing activity at all as "−". "NT" means that no test was conducted.

In the MRC-5 infection system, among 21 clones of body region-recognizing antibodies, 14 clones were strong neutralizing antibodies (+++) at 1 µg/mL or less in virus-neutralizing activity level as expressed by the 50% plaque-reducing concentration (IC50), 1 clone was a moderate neutralizing antibody (++) at 1-10 µg/mL, 3 clones were weak neutralizing antibodies (+) at 10-100 µg/mL, and 3 clones were nonneutralizing antibodies (−) showing no neutralizing activity at all at 100 µg/mL.

Meanwhile, among 44 clones of head region-recognizing antibodies, there was no strong neutralizing antibody (+++), 2 clones were moderate neutralizing antibodies (++), 4 clones were weak neutralizing antibodies (+), as well as 6 clones were those having a plaque-reducing rate of less than 50% at 100 µg/mL, but showing a slight neutralizing tendency (+/−) and 32 clones were nonneutralizing antibodies (−) showing no neutralizing activity at all.

In the results of the virus-neutralizing activity (50% focus count-reducing concentration) of the 28 clones examined in the ARPE infection system, clones showing neutralizing activity in the MRC-5 infection system generally exhibited a tendency of showing neutralizing activity in the ARPE infection system too, but there were present in part those that show neutralizing activity only in one system, those showing neutralizing activity in both systems, but having greatly different activity levels, and the like.

Based on the foregoing, it was confirmed that most of the antibodies that recognize the head region are nonneutralizing antibodies and most of the antibodies that recognize Domain I and Domain II which are the body region are strong neutralizing antibodies.

Example 5 Reactivity Analysis Between Variants and Each of the gB Antibodies <Preparation of Variants>

The present inventors considered neutralizing epitopes that induce neutralizing antibodies to be useful epitopes and nonneutralizing epitopes that induce nonneutralizing antibodies to be harmful, useless epitopes. Accordingly, to deimmunize nonneutralizing epitopes present in the head region, roughly two strategies were made to design modified gB antigens.

The first strategy is modification of gB by addition of N-sugar chain. Unlike O-sugar chains, N-sugar chains are given to the sequence NXT or NXS, which is a consensus sequence. Antibodies are hard to be produced for glycopeptides and the more bulky a sugar chain is, the harder it is for antibodies to be produced in its surrounding areas (The Journal of Immunology, 1997, 159 279-289). While the head region in CMV gB is considered as a region important for binding to its receptor, it is located at the farthest position from the viral membrane surface and exposed on the surface, making it easy for antibodies to bind thereto. In fact, it has been reported that many antibodies that recognize Domain IV, which is a part of the head region, are contained in human serum. (Non Patent Literature 7) Therefore, it was decided to introduce N-sugar chain into nonneutralizing epitopes in Domain IV and Domain III in the head region.

Meanwhile, Domain I, which is a part of the body region, is located in the base of gB and is an important region for the fusion with the host cell; however, a region that would otherwise be in contact with the viral membrane surface may be exposed on the surface if only ectodomain is expressed. To avoid this, modification to delete the exposed region (Fusion Loop portion) was made.

The second strategy is deletion of a part of the head region. Variants according to this strategy were prepared. Prepared variants and expression amounts thereof are shown in Table 6. As a method of preparation, ectodomain (1-682aa) of gB derived from the strain AD169 in CMV was cloned into pCAGGS1-dhfr-neo, which is disclosed in International Publication No. WO 03/004647, similar to the method of preparation of a variant in Example 1. It was designed so that His tag was added to the C terminus of gB.

For expression, FreeStyle293 or Expi293 expression system (Life Technology Inc.) was used. The expression plasmid was transfected into cells and culture supernatant was collected in 4 to 6 days. The culture supernatant containing modified CMV gB was subjected to purification using Ni-NTA Agarose (QIAGEN N.V. Cat. 30230) to obtain a purified modified CMV gB. The protein yield per 1 mL culture supernatant is summarized as expression amount in Table 6. The binding activity of the purified modified CMV gB was evaluated by ELISA.

In the four kinds of variants VC5, VC6, VC11, and VC15, among the prepared modified CMV gB, the expression amount was reduced, and degradation products or aggregates were increased, in comparison with a variant in which no mutation is introduced. It is considered that this is because the maintenance of the original gB conformation (trimer) became difficult by introducing one sugar chain, reducing the expression amount, and they were degraded by protease at the time of expression and preparation. Therefore, the evaluation by ELISA was not conducted for VC5, VC6, VC11, VC15.

TABLE 6

Prepared variants and expression amounts thereof

| Name of variant | Modification | Expression amount (μg/mL) |
|---|---|---|
| gB1-682-fm3M v9 | I132H, Y133R, T215E, W216A, R432T, R434Q | 30.6 |
| VC5 | I132H, Y133R, T215E, W216A, R432T, R434Q, D180N, S181A, Y182T | 3.4 |
| VC6 | I132H, Y133R, T215E, W216A, R432T, R434Q, S545N, P546S, G547S | 5.6 |
| VC7 | I132H, Y133R, T215E, W216A, R432T, R434Q, K609N, R610T, M611T | 16.8 |
| VC9 | I132H, Y133R, T215E, W216A, R432T, R434Q, K543N | 35.2 |
| VC10 | I132H, Y133R, T215E, W216A, R432T, R434Q, E544N, P546T | 25.1 |
| VC11 | I132H, Y133R, T215E, W216A, R432T, R434Q, G579N, H581T | 2.6 |
| VC12 | I132H, Y133R, T215E, W216A, R432T, R434Q, G579N, H581S | 19.1 |
| VC13 | I132H, Y133R, T215E, W216A, R432T, R434Q, L588N, P589A | 28.0 |
| VC14 | I132H, Y133R, T215E, W216A, R432T, R434Q, L588N, P589G | 32.3 |
| VC15 | I132H, Y133R, T215E, W216A, R432T, R434Q, V604N, Y606T | 8.2 |
| VC16 | I132H, Y133R, T215E, W216A, R432T, R434Q, D605N, L607T | 23.6 |
| VC22 | I132H, Y133R, T215E, W216A, R432T, R434Q, Q74N | 9.9 |
| VC23 | I132H, Y133R, T215E, W216A, R432T, R434Q, D77N, I79T | 11.2 |
| VC24 | I132H, Y133R, T215E, W216A, R432T, R434Q, E544N, P546T, L588N, P589G, K609N, R610T, M611T | 12.1 |
| VC31 | I132H, Y133R, T215E, W216A, R432T, R434Q, E544N, P546T, L588N, P589G, K609N, R610T, M611T, D77N, I79T | 13.6 |
| VC33 | I132H, Y133R, T215E, W216A, R432T, R434Q, E544N, P546T, L588N, P589G | 18.2 |
| VC37 | I132H, Y133R, T215E, W216A, R432T, R434Q, E544N, P546T, L588N, P589G, K609N, R610T, M611T, D77N, I79T, ΔS128-L138, ΔW216-Y218, and a glycine linker (GGG) was introduced and linked between R127-G139 | 21.2 |

TABLE 6-continued

Prepared variants and expression amounts thereof

| Name of variant | Modification | Expression amount (μg/mL) |
|---|---|---|
| VC39 | I132H, Y133R, W216A, T215E, R432T, R434Q, E544N, P546T, L588N, P589G, ΔS128-L138, ΔW216-Y218, and a glycine linker (GGG) was introduced and linked between R127-G139 | 40.4 |
| VC40 | I132H, Y133R, W216A, T215E, R432T, R434Q, E544N, P546T, L588N, P589G, D77N, I79T, ΔS128-L138, ΔW216-Y218, and a glycine linker (GGG) was introduced and linked between R127-G139 | 55.1 |
| gB1-682-fm3M Del21 | T215E, R432T, R434Q, ΔS128-L138, ΔW216-Y218, and a glycine linker (GGG) was introduced and linked between R127-G139 | 29.3 |
| D1D2 | gB97-468-GGGSGSGGG-631-682 (Y131A, I132A, Y133A, W216A, R432, R434Q) | 33.7 |
| (D1D2) × 2 | Two gB97-468-GGGSGSGGG-631-682 (Y131A, I132A, Y133A, W216A, R432, R434Q) were linked with a linker (GGGGSGGGGS) | 16.2 |
| (D1'D2) × 2 | Two gB97-468-GGGSGSGGG-631-682 (R432, R434Q, ΔS128-L138, ΔA216-Y218, and a glycine linker (GGG) was introduced and linked between R127-G139) were linked with a linker (GGGGSGGGGS) | 13.5 |

<Competition ELISA with Variant and Antibody>

Each purified variant was diluted to 1 μg/mL with PBS (SIGMA) and the purified variants were immobilized by transferring 50 μL into a MaxiSorp plate (Nunc) and incubating at 4° C. overnight. After the immobilization, the plate was washed with PBS and 100 μL each of the antibodies evaluated in Example 4 was added to a well in the plate, which was incubated at room temperature. One hour later, the plate was washed with PBST and 100 μL of the detection antibody anti-human IgG Fc/HRP (Rockland Immunochemicals, Inc. Cat. 709-1317) was added into the well in the plate, which was incubated at room temperature. One hour later, color development was performed by washing with PBST and adding 100 μL of TMB (SIGMA Cat. T-4444) to the well in the plate. 30 minutes later, the reaction was stopped with 1 N sulfuric acid and the color value (O.D. 450 nm/650 nm) was measured with a microplate reader (Molecular Devices, LLC). The results of the measurement are shown in Table 7 and Table 8.

TABLE 7

Reactivity of body region-recognizing antibodies

| | P12 | Q25 | N80 | Q5 | S68 | 7-2-66 | 8-2-12 | N79 |
|---|---|---|---|---|---|---|---|---|
| gB1-682-fm3Mv9 | + | + | + | + | + | + | + | + |
| VC7 | + | + | + | + | + | + | + | + |
| VC9 | + | + | + | + | + | + | + | + |
| VC10 | + | + | + | ± | + | + | + | + |
| VC12 | + | + | + | + | + | + | + | + |
| VC13 | + | + | + | + | + | + | + | + |
| VC14 | + | + | + | + | + | + | + | + |
| VC16 | + | + | + | + | + | + | + | + |
| VC22 | + | + | + | + | + | + | + | + |
| VC23 | + | + | + | + | + | + | + | + |
| VC24 | + | + | + | + | + | + | + | + |
| VC31 | + | + | + | + | + | + | + | + |
| VC33 | + | + | + | + | + | + | + | + |
| VC37 | + | + | + | + | ± | + | + | + |
| VC39 | + | + | ± | + | ± | + | + | + |
| VC40 | + | + | + | + | ± | + | + | + |
| Del21 | + | + | + | + | + | + | + | + |
| D1D2 | ± | ± | ± | ± | ± | ± | ± | + |
| (D1D2) × 2 | + | + | + | + | ± | + | + | + |

TABLE 8

Reactivity of head region-recognizing antibodies

| | J9 | K29 | S80 | J92 | K74 | 1-3-13 | M33 | 2-3-4 | R18 | J19 | R47 | J47 | P40 | Q92 | K17 | J82 | N66 | J61 | K61 | J58 | N93 |
|---|---|---|---|---|---|---|---|---|---|---|---|---|---|---|---|---|---|---|---|---|---|
| gB1-682-fm3Mv9 | + | + | + | + | + | + | + | + | + | + | + | + | + | + | + | + | + | + | + | + | + |
| VC7 | + | − | − | − | − | − | ± | + | − | + | − | + | + | + | + | − | ± | + | + | + | + |
| VC9 | + | + | + | + | + | + | + | + | + | + | + | − | + | + | + | + | + | + | + | + | + |
| VC10 | + | + | + | + | + | + | + | + | + | + | + | − | + | + | + | − | ± | − | − | − | ± |
| VC12 | + | + | + | + | + | + | + | + | + | + | + | − | ± | − | − | − | − | + | + | ± | − |
| VC13 | + | + | + | + | + | + | + | + | + | + | + | + | ± | − | − | − | − | − | + | − | − |
| VC14 | + | + | + | + | + | + | + | + | + | + | + | + | + | − | − | − | − | − | + | − | − |
| VC16 | + | + | + | + | + | + | + | + | + | + | + | + | + | − | − | − | + | + | ± | ± | |
| VC22 | + | − | − | + | + | + | + | + | + | + | + | + | + | + | + | + | + | + | + | + | + |
| VC23 | − | − | − | + | + | + | + | + | + | − | ± | + | + | + | + | + | + | + | + | + | + |
| VC24 | + | − | − | − | − | − | + | + | − | + | − | − | ± | ± | + | − | − | − | − | − | − |
| VC31 | − | − | − | − | − | − | ± | ± | − | ± | − | − | − | − | − | − | − | − | − | − | − |
| VC33 | + | + | + | + | + | + | + | + | + | + | − | ± | ± | − | − | − | − | − | − | − | − |
| VC37 | − | − | − | − | − | − | ± | ± | − | ± | − | − | − | − | − | − | − | − | − | − | − |
| VC39 | + | + | + | + | + | + | + | + | + | + | − | ± | ± | − | − | − | − | − | − | − | − |
| VC40 | − | − | − | + | + | + | + | + | + | ± | − | ± | − | − | − | − | − | − | − | − | − |
| Del21 | + | + | + | + | + | + | + | + | + | + | + | + | + | + | + | + | + | + | + | + | + |

TABLE 8-continued

Reactivity of head region-recognizing antibodies

| | J9 | K29 | S80 | J92 | K74 | 1-3-13 | M33 | 2-3-4 | R18 | J19 | R47 | J47 | P40 | Q92 | K17 | J82 | N66 | J61 | K61 | J58 | N93 |
|---|---|---|---|---|---|---|---|---|---|---|---|---|---|---|---|---|---|---|---|---|---|
| D1D2 | − | − | − | − | − | − | − | − | − | − | − | − | − | − | − | − | − | − | − | − | − |
| (D1D2) × 2 | − | − | − | − | − | − | − | − | − | − | − | − | − | − | − | − | − | − | − | − | − |

The reactivity analysis of prepared variants VC7, VC9, VC10, VC12, VC13, VC14, and VC16 was conducted. As control, gB1-682-fm3M v9 was used. As a result, the reactivity with K29, S80, J92, K74, 1-3-13, R18, R47, J82, which are head region-recognizing antibodies, was disappeared by introducing the K609N, R610T, and M611T mutations in VC7 and VC9 has similarly lost the reactivity with J47 by introducing the mutation K543N and VC10 has lost the reactivity with J47, J82, J61, K61, J58 by introducing the mutations E544N and P546T.

The variants VC11 and VC12 are the same in the modification amino acid sites. However, when the mutations G579N and H581T were introduced to VC11 and the mutations G579N and H581S were introduced to VC12, in consideration of steric hindrance and structural distortion due to addition of sugar chain, a decrease in expression amount and the increase of aggregates were found in VC11, but the trimer structure was maintained and the reactivity with the antibodies J47, Q92, K17, J82, N66, N93 was lost in VC12.

The variants VC13 and VC14 are the same in the modification amino acid sites. However, for the purpose of maintenance of the structure by changing P589 where it is easy to set an angle into Gly having high flexibility, the mutations L588N and P589A were introduced to VC13 and the mutations L588N and P589G were introduced to VC14. As a result, there were hardly any differences in the expression amount and properties and the reactivity with the antibodies K17, J82, N66, J61, J58, N93 was lost in both.

In the variants VC15 and VC16, sugar chains were introduced to neighboring amino acids in consideration of structural change by the sugar chain added sites and they were compared. When the mutations V604N and Y606T were introduced to VC15 and the mutations D605N and L607T were introduced to VC16, the decrease in expression amount and the increase of aggregates were found in VC15. In VC16, the trimer structure was maintained and the reactivity with the antibodies K17, J82, N66 was lost.

The variant VC22 has lost the reactivity with the antibodies K29 and S80 by introducing the mutation Q74N and VC23 has lost the reactivity with J9, K29, S80, J19 by introducing the mutations D77N and I79T.

The variant VC33 has lost the reactivity with the antibodies J47, K17, J82, N66, J61, K61, J58, N93 by introducing the VC10 mutations (E544N, P546T) and the VC14 mutations (L588N, P589G). This matches the antibody masked when each one sugar chain of VC10 and VC14 is introduced and indicates that masking of epitopes with sugar chains is successful with the structure maintained even if a plurality of sugar chains is introduced.

The variant VC24 has lost the reactivity with the antibodies K29, S80, J92, K74, 1-3-13, R18, R47, J47, K17, J82, N66, J61, K61, J58, N93 by introducing the VC7 mutations (K609N, R610T, M611T) and the VC10 mutations (E544N, P546T) and the VC14 mutations (L588N, P589G).

The variant VC31 has lost the reactivity with the antibodies J9, K29, S80, J92, K74, 1-3-13, R18, R47, J47, P40, Q92, K17, J82, N66, J61, K61, J58, N93 by introducing the VC7 mutations (K609N, R610T, M611T), the VC10 mutations (E544N, P546T), the VC14 mutations (L588N, P589G), and the VC23 mutations (D77N, I79T). In VC31, among the antibodies which are masked when each one sugar chain of VC7, VC10, VC14, and VC23 is introduced, the reduction level of the reactivity of the J19 antibody was low. Moreover, the reactivity of P40 and Q92, which each by itself had no reduction in reactivity, was reduced and it is considered that further elimination of epitopes occurred by exposure of epitopes and the bulkiness of sugar chain due to a slight structural change by increasing the number of sugar chain to introduce.

The variant VC39 has lost the reactivity with the antibodies J47, K17, J82, N66, J61, K61, J58, N93 by introducing the VC10 mutations (E544N, P546T) and the VC14 mutations (L588N, P589G) on the basis of gB1-682-fm3M Del21 with Fusion Loop1 and 2 deleted. This matches the case when each one sugar chain of VC10 and VC14 is introduced. Moreover, this also matches an antibody in which the reactivity is reduced in VC31 in which the two of the V10 mutation and the VC14 mutation were introduced on the basis of gB1-682-fm3M v9. Based on these, it was found that masking of epitopes with sugar chains was successful with the structure maintained even if the Fusion Loop portion is deleted and further multiple sugar chains are introduced.

The variant VC40 has lost the reactivity with the antibodies J9, K29, S80, J47, Q92, K17, J82, N66, J61, K61, J58, N93 by introducing the VC10 mutations (E544N, P546T), the VC14 mutations (L588N, P589G), and the VC23 mutations (D77N, I79T) on the basis of gB1-682-fm3M Del21. In comparison with one in which each one of the sugar chains of VC10, VC14, and VC23 is introduced, the reactivity with antibodies is generally matched, but the reactivity with J19, with which the reactivity was eliminated with only the sugar chains of VC23 by itself, was maintained in VC40. Moreover, the reactivity of Q92 with which the reactivity was maintained in VC10, VC14, VC23 was eliminated in VC40. For this, like VC31, it is considered that further elimination of epitopes occurred by exposure of epitopes and the bulkiness of sugar chain due to a slight structural change by increasing the number of sugar chain to introduce.

The variant VC37 has lost the reactivity with the antibodies J9, K29, S80, J92, K74, 1-3-13, R18, R47, J47, P40, Q92, K17, J82, N66, J61, K61, J58, N93 by introducing the VC7 mutations (K609N, R610T, M611T), the VC10 mutations (E544N, P546T), the VC14 mutations (L588N, P589G), and the VC23 mutations (D77N, I79T) on the basis of gB1-682-fm3M Del21. This matches an antibody in which the reactivity is reduced in VC31 in which the mutations of VC7, VC10, VC14, and VC23 were introduced on the basis of gB1-682-fm3M v9.

The variant D1D2 was created by removing a part of the head region containing Domain IV in consideration of conformation, linking 468 from gB97 and 682 from gB631 with a GGGSGSGGG linker (SEQ ID NO: 2), and furthermore introducing the amino acid modification Y131A, 1132A, Y133A, W216A in the Fusion Loop portion and the amino acid modification R432T, R434Q in the Furin cleavage site. An expression amount equivalent to gB1-682 was kept while maintaining the trimer structure by not only linking Domain I and Domain II, which are the body region, but also leaving Domain V, which is to be the center of the trimer, and furthermore modifying amino acids in the Fusion Loop portion. Moreover, when the reactivity analysis ELISA with the already obtained antibodies was performed, the reactivity with head region-recognizing antibodies was eliminated, while maintaining the reactivity with eight kinds of body region-recognizing antibodies.

The variant (D1D2)×2 was created by linking two D1D2 with the linker GGGGSGGGGS (SEQ ID NO: 3) and (D1'D2)×2 was created by deleting Fusion Loops 1 and 2 in (D1D2)×2. When the reactivity analysis ELISA of (D1D2)×2 and (D1'D2)×2 with the already obtained antibodies was performed, the reactivity with head region-recognizing antibodies was eliminated, while maintaining the reactivity with eight kinds of body region-recognizing antibodies.

Example 6 Guinea Pig Immunogenicity Test and Analysis of Immune Refocusing of Variant Antigens The evaluation of ability to induce antibodies of head region and body region in variant VC31, VC33, VC37, VC39, VC40, D1D2 and (D1D2)×2 prepared in Example 5 was performed by ELISA.

<Preparation of Immune Sera>

Guinea pigs were immunized with the variant gB1-682-fm3M v9, VC31, VC33, VC37, VC39, VC40, D1D2, and (D1D2)×2 prepared in Example 5 as antigens. As a contrast, gB1-682-fm3M v9 was used as an alternative antigen for wild type gB antigens. Each antigen was adjusted with physiological saline (Otsuka Pharmaceutical Co., Ltd.) to 0.2, 1, and 5 µg/animal and 10 v/v % Alum (Invivogen) and 50 µg/animal of CpG ODN1826 (Invivogen) were used as adjuvant. The adjusted antigen solutions were inoculated intramuscularly (100 µL/both hind limbs) into Hartley guinea pigs (female 3 animals/group) three times at 2-week intervals and whole blood was collected by cardiac puncture under isoflurane inhalation anesthesia 2 weeks after the final immunization. The obtained blood was separated into serum in a separation tube containing a setting accelerator. Using this serum, activity of inducing binding antibody titer against gB1-682-fm3M v9 (anti-gB ELISA) was evaluated.

<Measurement of Activity of Inducing Binding Antibody Titer by ELISA> gB1-682 fm3M v9 or D1D2 antigen was diluted to 1 µg/mL with PBS (SIGMA) and the antigen was immobilized by transferring 50 µL into a MaxiSorp plate (Nunc) and incubating at 4° C. overnight. After the immobilization, the plate was washed with PBS and the obtained gB antigen immune serum was serially diluted with PBS and 100 µL was added to a well in the plate, which was incubated at room temperature. One hour later, the plate was washed with PBST and 100 µL of the detection antibody anti-human IgG Fc/HRP (Rockland Immunochemicals, Inc. Cat. 709-1317) was added into the well in the plate, which was incubated for at room temperature. One hour later, color development was performed by washing with PBST and adding 100 µL of TMB (SIGMA Cat. T-4444) to the well in the plate. 30 minutes later, the reaction was stopped with 1 N sulfuric acid and the color value (O.D. 450 nm/650 nm) was measured with a microplate reader (Molecular Devices, LLC).

For the immune sera against the variant antigens VC31, VC33, VC37, VC39, VC40, D1D2, and (D1D2)×2, whether immune refocusing is induced or not was analyzed by ELISA in which gB1-682-fm3M v9 and D1D2 with deletion of Domain IV are each immobilized.

The results are shown in FIGS. 1-7 and, in FIGS. 1-7, (a) illustrates the results of ELISA in which gB1-682-fm3M v9 is immobilized, and (b) illustrates the results of ELISA in which D1D2 is immobilized. While any of the immune sera to VC31, VC33, VC37, VC39, VC40, D1D2 and (D1D2)×2 exhibited, in comparison with immune serum to gB1-682-fm3M v9, equivalent or rather lower binding antibody activity against gB1-682-fm3M v9, their binding antibody activity against D1D2 was increased and it was confirmed that the antibody population (proportion of antibody group) against the body region was increased.

It is considered that this result is a result of more efficient and effective induction of immune responses to neutralizing epitopes (useful epitopes) remaining on the body region, which is an important region, by attempting to deimmunize nonneutralizing epitopes (harmful and useless epitopes) by N-sugar chain introduction to Domain III or Domain IV, which are parts of the head region of the CMV gB antigen, or deletion mutation of the head region containing Domain IV. In other words, it is considered that biased immune responses (immune deviation) to CMV gB antigens was able to be corrected (immune correction) to an ideal form by the immune refocusing strategy.

Example 7 Neutralization Test Using Guinea Pig Antiserum Against Variant Antigens Using (D1'D2)×2 immune serum, in addition to VC31, VC37, VC40, and (D1D2)×2 immune sera prepared in Example 6, the activity to induce neutralizing antibodies (plaque count reducing rate) in the fibroblast cell line and the epithelium cell line was evaluated.

<Strain CMV AD169/Fibroblast Cell Neutralization Test>

The analysis of neutralizing antibody titer using fibroblast cells was conducted using the activity of reducing the number of foci (focus reduction activity). For the analysis, plates obtained by culturing overnight MRC-5 cells seeded onto black wall 96 well plates (Corning 3340) processed with CellBIND or sell carrier-96 Ultra Collagen coated plates (PerkinElmer 6055700) at $2 \times 10^4$ cells/well were used. Each immune serum was serially diluted to adjust the concentration to a predetermined concentration and mixed with the strain CMV AD169 at about 100-1000 PFU and then reacted at 37° C. for one hour. Cells in the analytic plates were inoculated with the reaction solution at 30 µL/well and then centrifugation at 400×g was performed at room temperature for 30 minutes and the virus was adsorbed onto the cells. The reaction solution was removed and washing with an FBS free medium was conducted once and then culturing in the medium containing 2% FBS was conducted for 16-20 hours. After the culture, inactivation and fixation of cells with 50% acetone/PBS were performed at room temperature for 20 minutes. Subsequently, this was treated at room temperature with 0.1% Triton-X100 for 10 minutes and, after washing, a 1 µg/mL anti-CMV IE1-IE2 monoclonal antibody (CH160:Abcam ab53495, Santacruz sc-69748) was reacted at 37° C. for one hour. After washing, 1 µg/mL Goat Anti-Rabbit IgG H & L (Alexa Fluor® 488) (Abcam ab150077) was reacted at 37° C. for one hour, and after further washing, 1 µg/mL-Cellstain®-Hoechst 33342 solution (dojindo 346-07951) was reacted at room temperature for 10 minutes and PBS containing 0.5% BSA was added to a washed plate at 100 μL/well; images of each of the wells were taken in with ImageXpress micro (Molecular Devices); the number of cells that reacted with the CMV IE1-IE2 monoclonal antibody and the total number of cells were counted using the analytic software MetaXpress (Molecular Devices) and the proportion of the number of cells that reacted with the CMV IE1-IE2 monoclonal antibody to the total number of cells was calculated. Based on the proportion of the number of cells that reacted with the CMV IE1-IE2 monoclonal antibody when only the virus was added, the neutralizing activity was determined from the suppression rate (inhibition rate) of the proportion of the number of cells with each immune serum.

Figure 8:
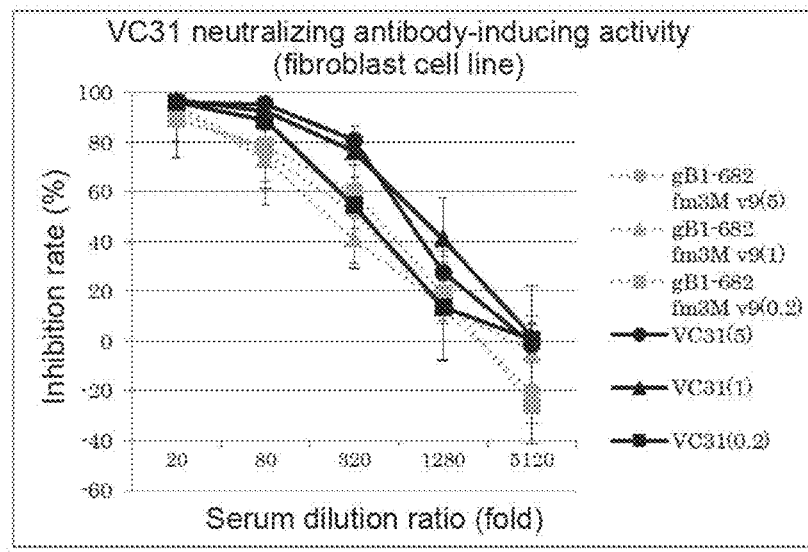
FIG. 8 illustrates a result of a neutralization test in a fibroblast cell system with immune sera against each of the modified CMV gB proteins in Example 7.
Figure 8:
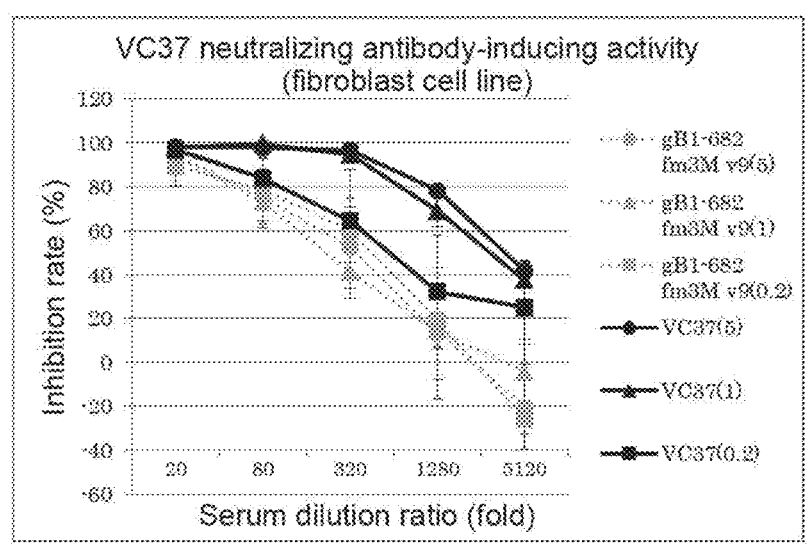
Figure 8:
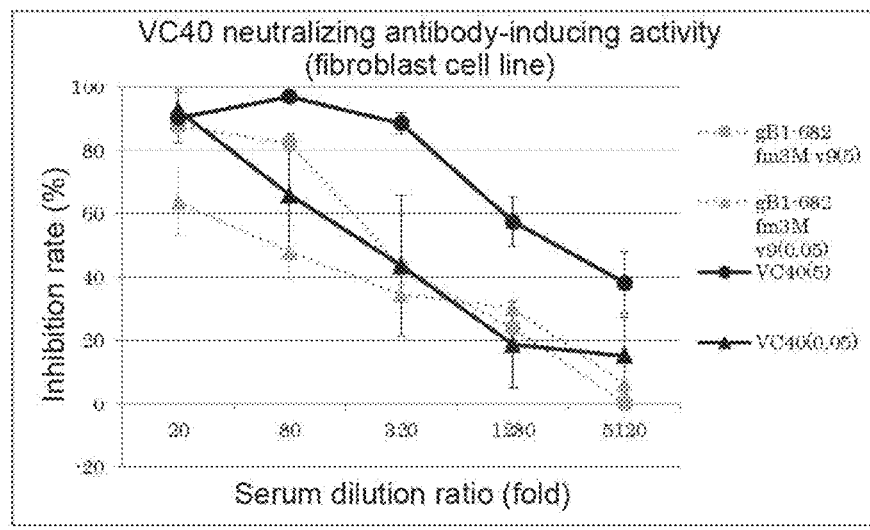
Figure 9:
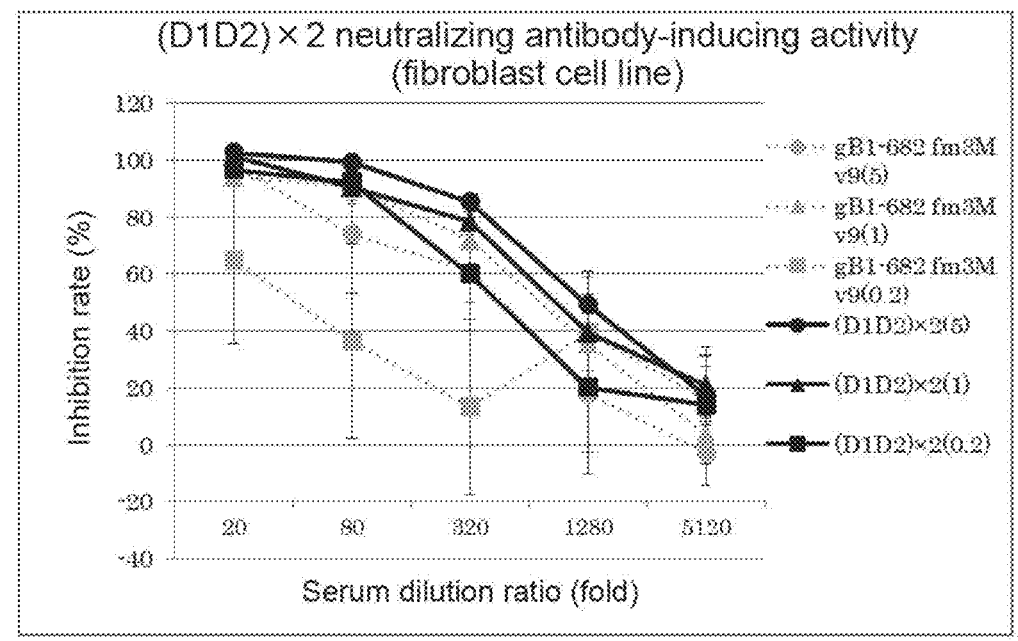
FIG. 9 illustrates a result of a neutralization test in a fibroblast cell system with immune sera against each of the modified CMV gB proteins in Example 7.
Figure 9:
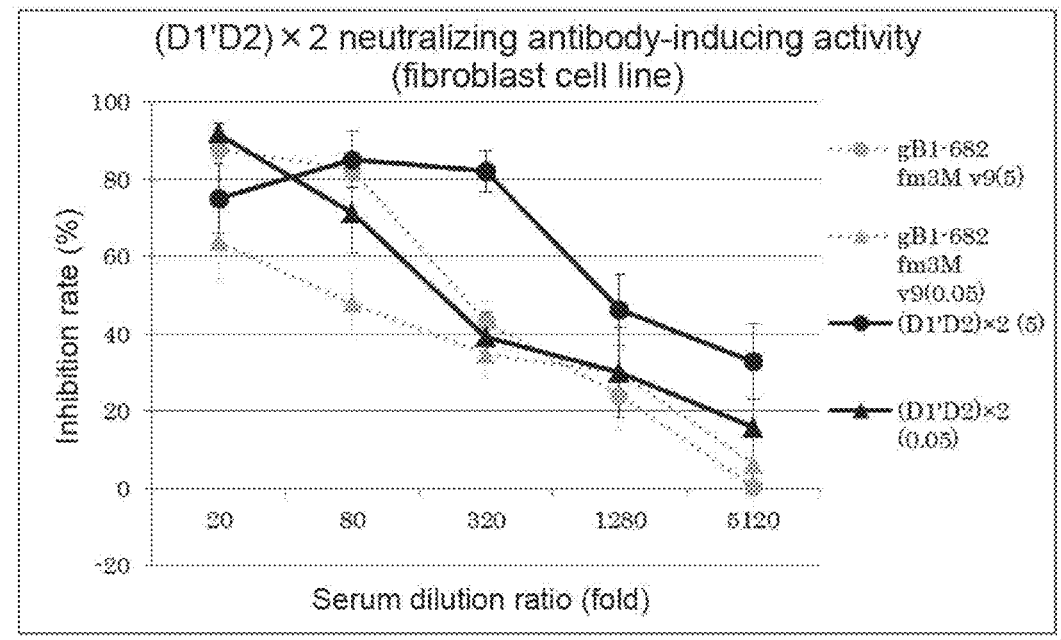

The results of neutralization tests in the fibroblast cell system are shown in FIGS. 8 and 9. In the graphs in FIGS. 8 and 9, the mean values of n=3 are plotted and +/−SE error bars are supplemented. It was confirmed that the immune sera of VC31, VC37, VC40, (D1D2)×2, and (D1'D2)×2 induced the neutralizing antibody activity higher than gB1-682-fm3M v9.

<CMV AD169rev/Epithelium Cell Neutralization Test>

The analysis of neutralizing antibody titer using epithelium cells was conducted using the activity of reducing the number of foci (focus reduction activity). For analysis, plates obtained by culturing overnight APRE-19 cells seeded into cell carrier-96 Ultra Collagen coated plates (PerkinElmer 6055700) at 2×10⁴ cells/well were used. As the virus, the strain AD169rev prepared in Example 4 was used. Each immune serum was serially diluted to adjust the concentration to a predetermined concentration and mixed with the strain CMV AD169rev at about 1000 PFU and then reacted at 37° C. for one hour. Cells in the analytic plates were inoculated with the reaction solution at 30 μL/well and then centrifugation at 400×g was performed at room temperature for 30 minutes and the virus was adsorbed onto the cells. The reaction solution was removed and washing with an FBS free medium was conducted once and then culturing in the medium containing 2% FBS was conducted for 16-20 hours. After the culture, inactivation and fixation of cells with 50% acetone/PBS were performed at room temperature for 20 minutes. Subsequently, this was treated at room temperature with 0.1% Triton-X100 for 10 minutes and, after washing, a 1 μg/mL anti-CMV IE1-IE2 monoclonal antibody (CH160: Santacruz sc-69748) was reacted at 37° C. for one hour. After washing, 1 μg/mL Goat Anti-Rabbit IgG H & L (Alexa Fluor® 488) (Abcam ab150077) was reacted at 37° C. for one hour, and after further washing, 1 μg/mL—Cellstain®-Hoechst 33342 solution (dojindo 346-07951) was reacted at room temperature for 10 minutes and PBS containing 0.5% BSA was added to a washed plate at 100 μL/well; images of each of the wells were taken in with ImageXpress micro (Molecular Devices); the number of cells that reacted with the CMV IE1-IE2 monoclonal antibody and the total number of cells were counted using the analytic software MetaXpress (Molecular Devices) and the proportion of the number of cells that reacted with the CMV IE1-IE2 monoclonal antibody to the total number of cells was calculated. Based on the proportion of the number of cells that reacted with the CMV IE1-IE2 monoclonal antibody when only the virus was added, the neutralizing activity was determined from the suppression rate of the proportion of the number of cells with the test substance.

Figure 10:
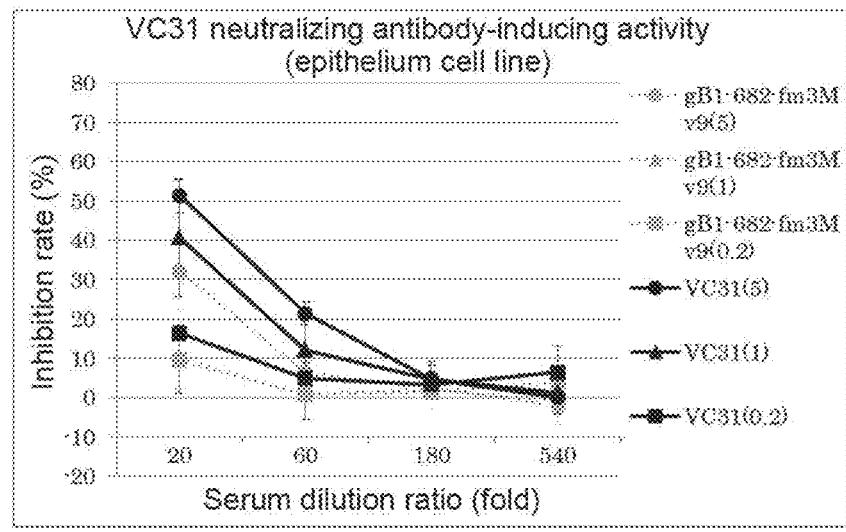
FIG. 10 illustrates a result of a neutralization test in an epithelium cell system with immune sera against each of the modified CMV gB proteins in Example 7.
Figure 10:
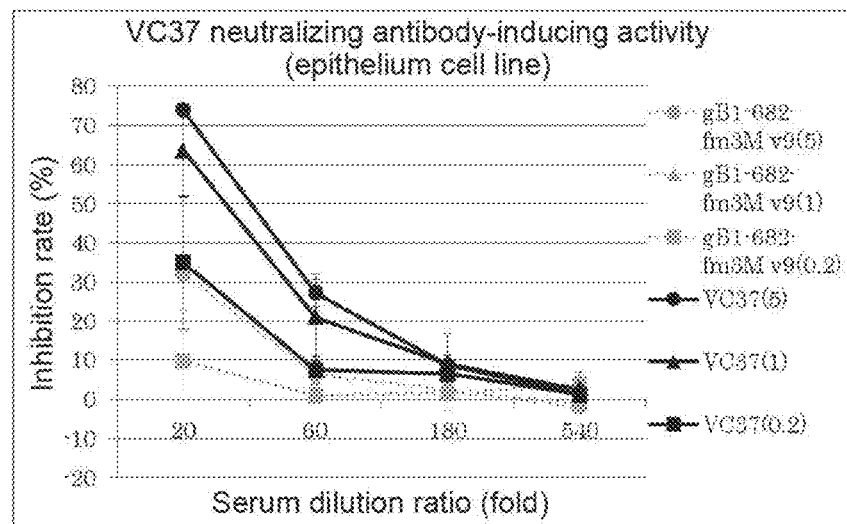
Figure 10:
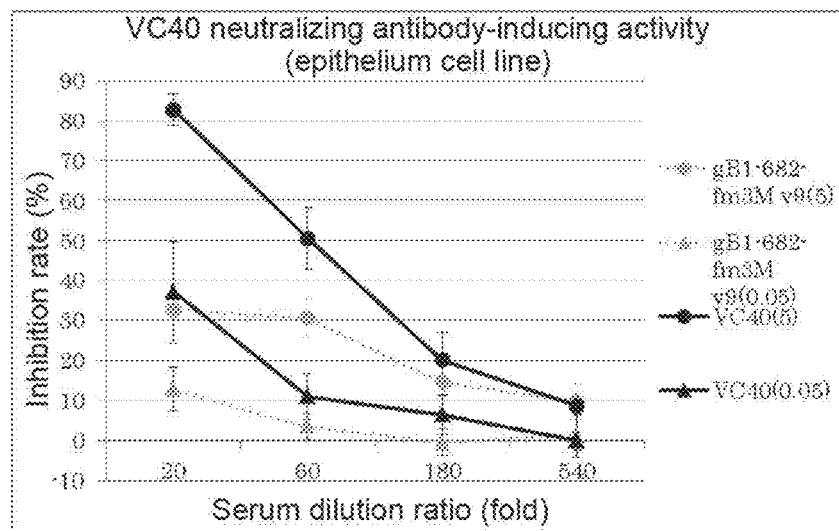
Figure 11:
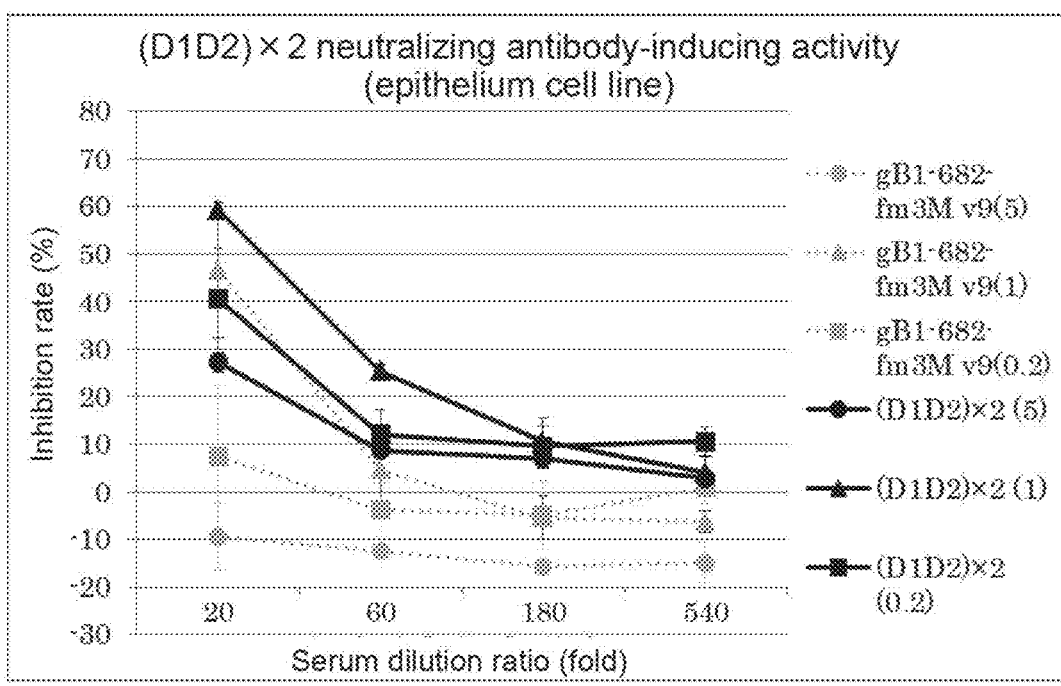
FIG. 11 illustrates a result of a neutralization test in an epithelium cell system with immune sera against each of the modified CMV gB proteins in Example 7.
Figure 11:
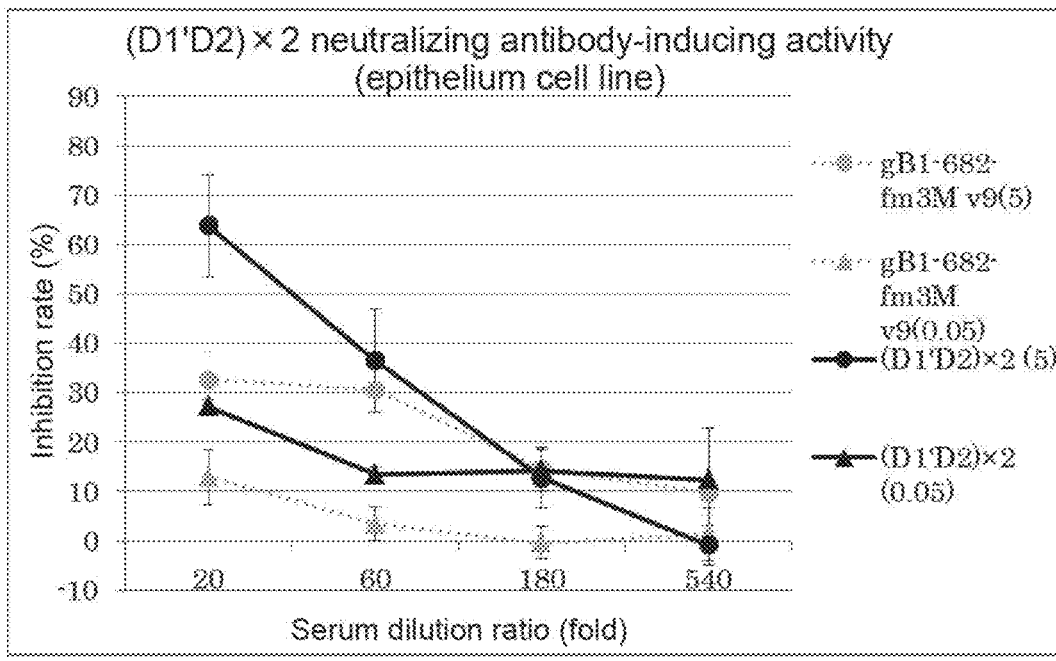

The results of epithelium cell line neutralization tests are shown in FIGS. 10 and 11. In the graphs in FIGS. 10 and 11, the mean values of n=3 are plotted and +/−SE error bars are supplemented. It was confirmed that the immune sera of VC31, VC37, VC40, (D1D2)×2, and (D1'D2)×2 induced the neutralizing antibody activity higher than gB1-682-fm3M v9.

It is considered that the foregoing results are a result of more efficient and effective induction of immune responses to neutralizing epitopes (useful epitopes) remaining on the body region, which is an important region, by attempting to deimmunize nonneutralizing epitopes (harmful and useless epitopes) by N-sugar chain introduction to Domain III or Domain IV, which are head region of the CMV gB antigen, or deletion mutation of Domain IV, which is a part of the head region. In other words, it may be said that biased immune responses (immune deviation) to CMV gB antigens was able to be corrected (immune correction) to an ideal form by the immune refocusing strategy.

INDUSTRIAL APPLICABILITY

The modified CMV gB protein according to the present invention can be used for preparation of vaccines effective in prevention and treatment of CMV infection.

The invention claimed is:

1. A modified CMV gB protein comprising a head region modified from a head region in an envelope glycoprotein B (CMV gB protein) in a wild type cytomegalovirus and having an improved ability to induce body region-recognizing antibodies, wherein the modification in the head region comprises modification by sugar chain introductions to at least 2 amino acid residues selected from the group consisting of amino acid residues at corresponding positions to the positions 77, 544. 588, and 609 in the amino acid sequence set forth in SEQ ID NO: 1.

2. The modified CMV gB protein according to claim 1, wherein the modification in the head region comprises modification by sugar chain introductions to at least 3 amino acid residues selected from the group consisting of amino acid residues at corresponding positions to the positions 77, 544, 588, and 609 in the amino acid sequence set forth in SEQ ID NO: 1.

3. The modified CMV gB protein according to claim 1, wherein the modification in the head region comprises modification by sugar chain introductions to amino acid residues at corresponding positions to the positions 77, 544, and 588 in the amino acid sequence set forth in SEQ ID NO: 1.

4. A The modified CMV gB protein according to claim 1, wherein the modification in the head region comprises modification by sugar chain introductions to amino acid residues at corresponding positions to the positions 77, 544, 588, and 609 in the amino acid sequence set forth in SEQ ID NO: 1.

5. The modified CMV gB protein according to claim 4, wherein the sugar chain is introduced by substitution of an amino acid residue at a corresponding position to the position 77 in the amino acid sequence set forth in SEQ ID NO: 1 with an asparagine residue and substitution of an amino acid residue at a corresponding position to the position 79 in the amino acid sequence set forth in SEQ ID NO: 1 with a threonine residue, substitution of an amino acid residue at a corresponding position to the position 544 in the amino acid sequence set forth in SEQ ID NO: 1 with an asparagine residue and substitution of an amino acid residue at a corresponding position to the position 546 in the amino acid sequence set forth in SEQ ID NO: 1 with a threonine residue, substitution of an amino acid residue at a corresponding position to the position 588 in the amino acid sequence set forth in SEQ ID NO: 1 with an asparagine residue and substitution of an amino acid residue at a corresponding position to the position 589 in the amino acid sequence set forth in SEQ ID NO: 1 with a glycine residue, and substitution of an amino acid residue at a corresponding position to the position 609 in the amino acid sequence set forth in SEQ ID NO: 1 with an asparagine residue, substitution of an amino acid residue at a corresponding position to the position 610 in the amino acid sequence set forth in SEQ ID NO: 1 with a threonine residue, and substitution of an amino acid residue at a corresponding position to the position 611 in the amino acid sequence set forth in SEQ ID NO: 1 with a threonine residue.

6. A CMV immunogenic composition comprising the modified CMV gB protein according to claim 1.

* * * * *